United States Patent
Dayton

(10) Patent No.: US 9,675,721 B2
(45) Date of Patent: Jun. 13, 2017

(54) DECONTAMINATION APPARATUS AND METHOD

(71) Applicant: Daylight Medical, Inc., Middleburg Heights, OH (US)

(72) Inventor: Roderick M. Dayton, Strongsville, OH (US)

(73) Assignee: Diversity, Inc., Charlotte, NC (US)

( * ) Notice: Subject to any disclaimer, the term of this patent is extended or adjusted under 35 U.S.C. 154(b) by 0 days.

(21) Appl. No.: 14/087,589

(22) Filed: Nov. 22, 2013

(65) Prior Publication Data

US 2014/0079587 A1   Mar. 20, 2014

Related U.S. Application Data

(63) Continuation of application No. PCT/US2012/067060, filed on Nov. 29, 2012.

(60) Provisional application No. 61/564,840, filed on Nov. 29, 2011, provisional application No. 61/595,140, filed on Feb. 5, 2012.

(51) Int. Cl.
*A61L 2/24*   (2006.01)
*A61L 2/10*   (2006.01)

(52) U.S. Cl.
CPC ...... *A61L 2/24* (2013.01); *A61L 2/10* (2013.01); *A61L 2202/121* (2013.01); *A61L 2202/14* (2013.01); *A61L 2202/24* (2013.01)

(58) Field of Classification Search
CPC ... D06F 59/04; A61L 2/10; A61L 9/20; A61L 2/24
USPC .................................................. 422/22, 24
See application file for complete search history.

(56) References Cited

U.S. PATENT DOCUMENTS

| | | | |
|---|---|---|---|
| 4,449,050 A | | 5/1984 | Kamhi |
| 4,877,964 A | | 10/1989 | Tanaka et al. |
| 5,225,172 A | | 7/1993 | Meyler et al. |
| 5,388,701 A | * | 2/1995 | Ridgeway ............... 206/583 |
| 5,446,289 A | | 8/1995 | Shodeen et al. |
| 5,688,475 A | * | 11/1997 | Duthie, Jr. ........... 422/186.3 |

(Continued)

FOREIGN PATENT DOCUMENTS

| | | |
|---|---|---|
| JP | 05008819 | 1/1993 |
| JP | 2001187625 | 7/2001 |

(Continued)

OTHER PUBLICATIONS

U.S. Appl. No. 61/537,731, Sep. 22, 2011.*

(Continued)

*Primary Examiner* — Regina M Yoo
(74) *Attorney, Agent, or Firm* — Cooper Legal Group, LLC

(57) ABSTRACT

Provided is an apparatus for disinfecting an object by at least partially removing a biologically-active contaminant there from. A housing encloses a disinfection chamber in which a portion of the object is to be received to be disinfected, and includes an inlet aperture through which the object is introduced to the apparatus. An ultraviolet light source emits ultraviolet light to be imparted on the portion of the object introduced to the disinfection chamber for deactivating at least a portion of the biologically-active contaminant present on the object. A controller controls operation of at least one of a feeder and the ultraviolet light to achieve a level of disinfection of the object, rendering the object suitable for use in a substantially-sterile application.

5 Claims, 16 Drawing Sheets

(56) References Cited

U.S. PATENT DOCUMENTS

| | | | |
|---|---|---|---|
| 5,786,598 | A | 7/1998 | Clark et al. |
| 5,894,130 | A | 4/1999 | Bach |
| 6,343,425 | B1* | 2/2002 | Sias et al. ............... 34/389 |
| 6,369,394 | B1 | 4/2002 | Lee |
| 6,475,433 | B2 | 11/2002 | McGeorge et al. |
| 6,566,659 | B1* | 5/2003 | Clark et al. ............. 250/455.11 |
| 6,592,816 | B1 | 7/2003 | Ebel et al. |
| 6,602,244 | B2* | 8/2003 | Kavanagh et al. ........... 604/544 |
| 6,605,260 | B1* | 8/2003 | Busted ..................... 422/186.3 |
| 6,673,137 | B1* | 1/2004 | Wen ................................ 96/224 |
| 6,730,923 | B1 | 5/2004 | May et al. |
| 7,234,586 | B1 | 6/2007 | Newman |
| 7,829,016 | B2 | 11/2010 | Deal et al. |
| 7,879,288 | B2 | 2/2011 | Brown-Skrobot |
| 8,710,460 | B2 | 4/2014 | Dayton |
| 2002/0146343 | A1 | 10/2002 | Jenkins |
| 2002/0168287 | A1* | 11/2002 | Eckhardt et al. ............... 422/24 |
| 2002/0192326 | A1 | 12/2002 | Powers et al. |
| 2002/0197478 | A1 | 12/2002 | Muggli |
| 2003/0085266 | A1* | 5/2003 | Simon ............................. 232/27 |
| 2003/0121839 | A1 | 7/2003 | Ryan, Jr. et al. |
| 2003/0122086 | A1 | 7/2003 | Ryan et al. |
| 2003/0150475 | A1 | 8/2003 | Abrams et al. |
| 2003/0155531 | A1* | 8/2003 | Clark et al. ............... 250/492.1 |
| 2005/0013729 | A1 | 1/2005 | Brown-Skrobot |
| 2005/0236579 | A1 | 10/2005 | Jenkins |
| 2005/0254992 | A1 | 11/2005 | Jenkins |
| 2007/0023710 | A1 | 2/2007 | Tom |
| 2007/0280867 | A1* | 12/2007 | Miller et al. .................. 422/300 |
| 2008/0085228 | A1 | 4/2008 | Yamazaki et al. |
| 2008/0175838 | A1 | 7/2008 | Schenk et al. |
| 2008/0199354 | A1* | 8/2008 | Gordon ........................... 422/24 |
| 2009/0252646 | A1 | 10/2009 | Holden |
| 2009/0280028 | A1 | 11/2009 | Muggli |
| 2010/0007492 | A1* | 1/2010 | Ressler et al. ................ 340/540 |
| 2010/0044582 | A1 | 2/2010 | Cooper |
| 2010/0198195 | A1* | 8/2010 | Nishtala et al. .............. 604/544 |
| 2011/0095205 | A1 | 4/2011 | Noto |
| 2011/0283661 | A1* | 11/2011 | Miller ............................. 53/425 |
| 2013/0078142 | A1* | 3/2013 | Gordon ........................... 422/24 |

FOREIGN PATENT DOCUMENTS

| | | |
|---|---|---|
| JP | 2007097692 A | 4/2007 |
| WO | 02/076513 A1 | 10/2002 |
| WO | 2008/008426 A2 | 1/2008 |
| WO | 2010/044748 A1 | 4/2010 |
| WO | 2010044748 | 4/2010 |
| WO | 2010/150045 A1 | 12/2010 |

OTHER PUBLICATIONS

"Vioguard Self-Sanitizing Keyboard Baths Itself in Ultraviolet Light to Kill the Germs" http://www.medgadget.com/2012/01/vioguard-self-sanitizing-keyboard-bathes-itself-in-ultraviolet-light-to-kill-the-germs.html. Article dated Jan. 4, 2012. Downloaded Oct. 25, 2013.
International Search Report for Application No. PCT/US2012/067060 dated Feb. 26, 2013.
Extended European Search Report dated Nov. 27, 2015 for EP 12853114.2.
Partial Supplementary European Search Report dated Apr. 17, 2015 for EP 12853114.2.
U.S. Appl. No. 14/531,319, filed Nov. 3, 2014.
U.S. Appl, No. 14/531,362, filed Nov. 3, 2014.
Japanese Office Action dated Dec. 6, 2016 for Application No. 2014-544884.

* cited by examiner

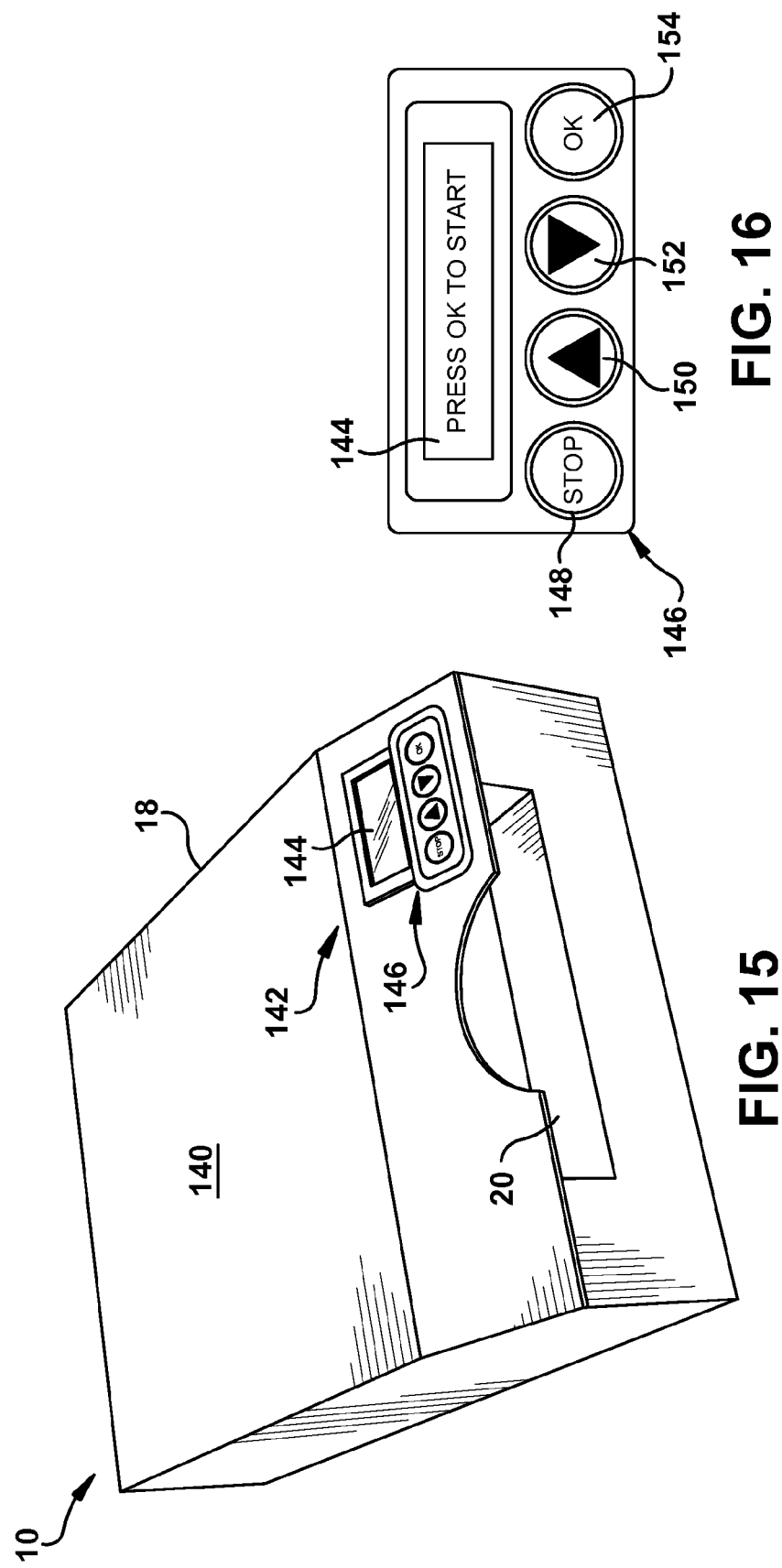

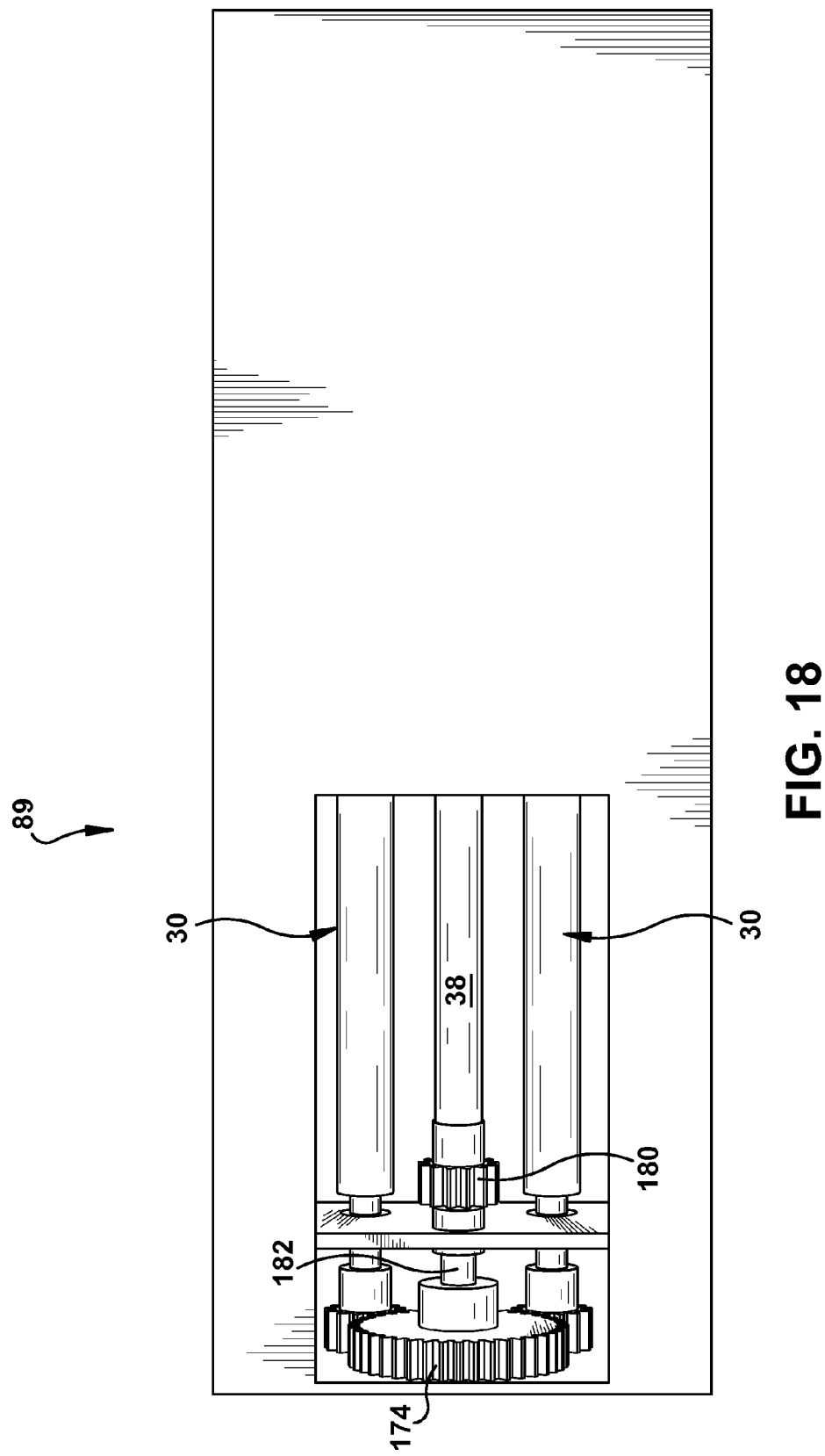

DECONTAMINATION APPARATUS AND METHOD

CROSS-REFERENCE TO RELATED APPLICATIONS

This application is a continuation of prior International Application No. PCT/US12/67060, filed Nov. 29, 2012, which claims the benefit of U.S. Provisional Application No. 61/564,840, filed Nov. 29, 2011, and U.S. Provisional Application No. 61/595,140, filed Feb. 5, 2012, each of which is incorporated in its entirety herein by reference.

BACKGROUND OF THE INVENTION

1. Field of the Invention

This application relates generally to a method and apparatus for reducing contagions on an object and, more specifically, to method and apparatus for suitably exposing an object to be used in a substantially-sterile environment to a disinfectant, which can optionally be a sterilizing agent.

2. Description of Related Art

Sterile, or at least substantially-sterile environments are common in the medical field for treating patients with minimal risk of infection. To avoid exposing patients in such environments to infectious organisms medical personnel working therein are required to take precautionary measures. All personnel are required to wash thoroughly before entering the environment, and wear items of clothing such as surgical scrubs that have been decontaminated.

Other objects such as medical equipment can also be contaminated with infectious organisms, and can pose a threat to introduce such organisms into the sterile environment. Bedding, medical devices, and virtually all other objects brought into a sterile environment must undergo sterilization procedures to minimize the risk of infection to patients. Labels for identifying medications, personal possessions, tissue samples, or any other object within a sterile environment are among the other objects that must also undergo a decontamination procedure. More recently, portable electronic devices such as tablet computers, for example, have become useful within sterile environments such as an operating room during a surgical procedure. The tablet computer can store a large volume of electronic images and other data that can be reproduced by the tablet computer without requiring separate hardcopies of each such image just in case one of the various different images is needed.

Traditionally, blank labels have been sterilized by the manufacturer and then sealed within an individual wrapper before the wrapped labels are distributed to hospitals or other end users. Likewise, pens that are to be used for hand writing label content on the blank, sterilized labels are also sterilized by the manufacturer and sealed in individual wrappers to be distributed to the users in the medical field along with the packaged and sterilized blank labels. In use, a blank label in its wrapper is retrieved from a bin storing such labels along with a wrapped pen. The wrappers enclosing both the label and the pen are opened by personnel within or near the sterile environment, and the label content is hand written onto the sterilized label using the sterilized pen. However, this traditional method and system for providing customized sterile labels in the medical field is prone to errors due to illegible handwriting and data omission.

Printing label content onto labels using a computer printer can help mitigate the problems posed by illegible handwriting and data omission. However, computer printers print label content onto label stock that is not suitably sterile for use in healthcare facilities upon completion of the printing process whereby the label content is applied to the label stock.

Electronic devices such as tablet computers and notebook computers, for example, pose additional problems when being considered for use in a medical environment. Their cases include apertures, seams, internal compartments and a variety of other structures where infectious organisms can hide from a disinfectant or sterilizing agent utilized as part of a decontamination process. Thus, even when exposed to such a decontaminant or sterilizing agent, infectious organisms hidden at such locations on an electronic device can be unknowingly transported into the sterile environment. There is no accepted sterilization method and apparatus that renders portable electronic devices such as tablet computers suitably sterile for use in a sterile environment.

BRIEF SUMMARY OF THE INVENTION

Accordingly, there is a need in the art for a method and apparatus for generating a machine-printed, substantially-sterile label on demand for use in medical applications.

According to one aspect, the subject application involves an apparatus for disinfecting an object by at least partially removing a biologically-active contaminant from the object. The apparatus includes a housing enclosing a disinfection chamber in which a portion of the object is to be received to be disinfected, and an inlet aperture through which the object is introduced to the apparatus. A feeder conveys the object introduced to the inlet aperture generally toward the disinfection chamber and discharges the object subsequent to disinfection of the object. An ultraviolet light source emits ultraviolet light to be imparted on the portion of the object introduced to the disinfection chamber for deactivating at least a portion of the biologically-active contaminant present on the object. A controller controls operation of at least one of the feeder and the ultraviolet light to achieve a level of disinfection of the object to render the object suitable for use in a substantially-sterile, and optionally medical application.

According to another aspect, the subject application involves a method of generating a label for use in a medical application. The method includes receiving label content specified by a user that is to be applied to a surface of the label. The label content comprising a machine-generated character is printed, on demand, onto the label, wherein the with the label content is dispensed in a non-sterile condition, is placed into a sterilizing sleeve, sterilized, and is then ready for use in the medical application.

According to another aspect, the label content comprising a machine-generated character is printed, on demand, onto the label, the label bearing the label content is dispensed in a non-sterile condition, the label is removed from its initial printing backing substrate and transferred onto a sterilizing carrier, placed into a sterilizing sleeve, sterilized, and is then ready for use in the medical application. The sterilizing carrier can include a release surface of a material that is substantially-transparent to UVC light. According to such an embodiment, both the exposed surface of the label bearing the label content and the adhesive backing of the label can be simultaneously or concurrently exposed to UVC light used as the sterilizing agent as discussed below.

According to another aspect, the subject application involves a printer accessory that is to cooperate with a printer for producing labels for use in a medical application. The printer accessory includes a receiver for receiving the label with label content printed, on demand and at a facility where the label is to be used in the medical application, and dispensed by the printer. The label content includes machine-generated characters. The label with the label content is manually introduced to a package that is to at least partially enclose the label, the label is then sterilized, and then dispensed in a substantially-sterile condition suitable for use in the medical application.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

BRIEF DESCRIPTION OF SEVERAL VIEWS OF THE DRAWING

The invention may take physical form in certain parts and arrangement of parts, embodiments of which will be described in detail in this specification and illustrated in the accompanying drawings which form a part hereof and wherein:

FIG. 15 shows a perspective view of a sterilizer with an inlet aperture through which an object is to be introduced to, and ejected from the sterilizer;

FIG. 16 shows a plan view of a user interface provided to a sterilizer;

FIG. 18 shows a bottom, partially-cutaway view of a cartridge to be provided to a sterilizer, the cartridge including an axle supporting a drive gear and an intermediate gear;

DETAILED DESCRIPTION OF THE INVENTION

Figure 1:
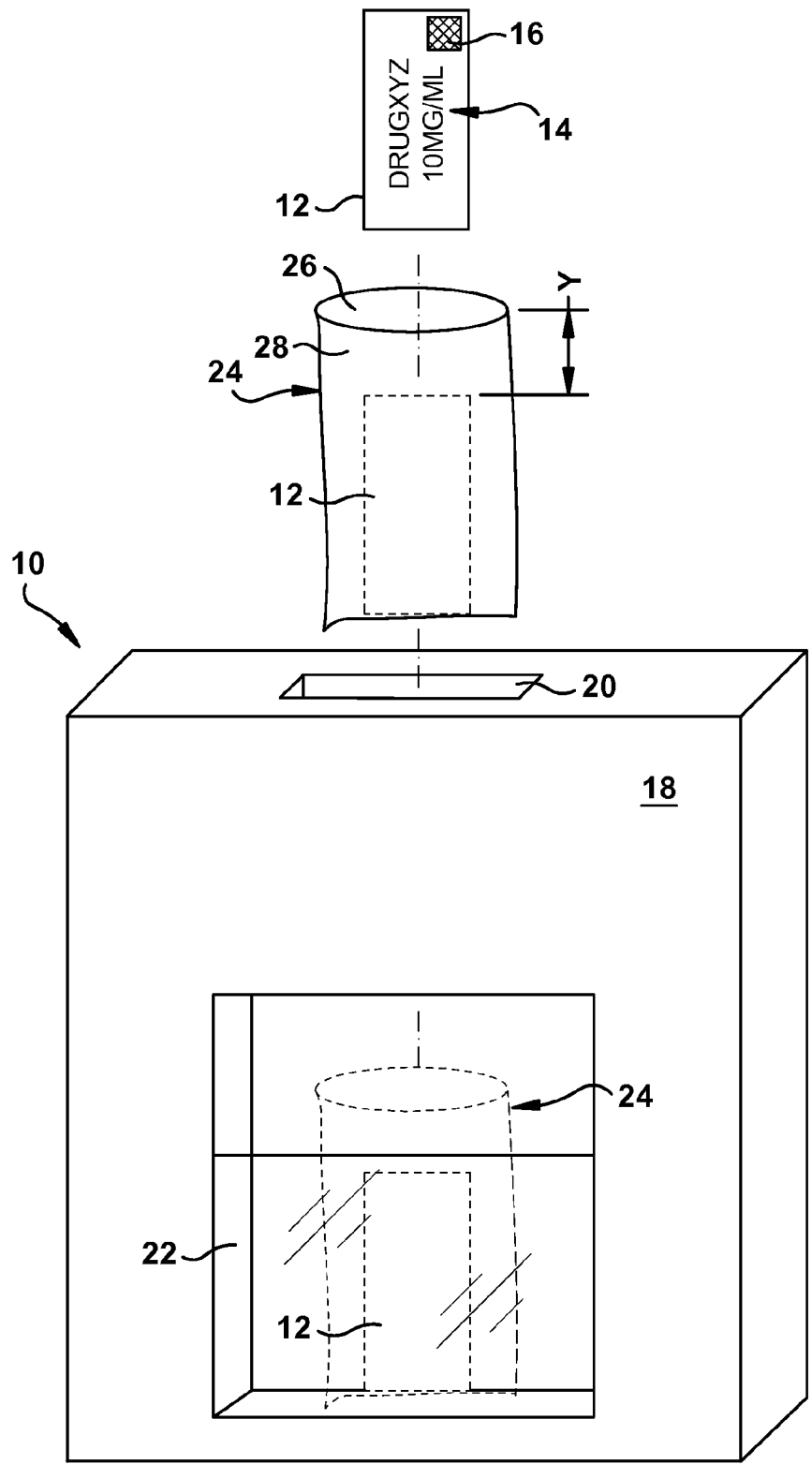
FIG. 1 shows a perspective view of an illustrative embodiment of a sterilizer.

Certain terminology is used herein for convenience only and is not to be taken as a limitation on the present invention. Relative language used herein is best understood with reference to the drawings, in which like numerals are used to identify like or similar items. Further, in the drawings, certain features may be shown in somewhat schematic form.

It is also to be noted that the phrase "at least one of", if used herein, followed by a plurality of members herein means one of the members, or a combination of more than one of the members. For example, the phrase "at least one of a first widget and a second widget" means in the present application: the first widget, the second widget, or the first widget and the second widget. Likewise, "at least one of a first widget, a second widget and a third widget" means in the present application: the first widget, the second widget, the third widget, the first widget and the second widget, the first widget and the third widget, the second widget and the third widget, or the first widget and the second widget and the third widget.

FIG. 1 provides a perspective view of an illustrative embodiment of a sterilizer 10 for subjecting a label 12 to a sterilization process. The sterilization process is performed by the sterilizer 10 on demand, as substantially-sterilized labels 12 are needed to label an object or substance in a medical application. Rendering the label 12 substantially sterile with the sterilizer 10 does not necessarily require the label 12 to be 100% sterile, free of any and all living organisms. Instead, to be substantially sterile there is a lower level of living contagions on the label 12 after performance of the sterilization process than existed on the label 12 prior to performance of the sterilization process. According to other embodiments, the label 12 is required to possess a lower level of living or otherwise biologically-active contagions than a threshold quantity permitted under U.S. Food and Drug Administration requirements on objects dedicated for use in a sterile field such as in an operating room during a surgical procedure. According to other embodiments, the sterilization process kills or otherwise eliminates at least 99% of all living or otherwise biologically-active contagions present on the label 12 immediately prior to performance of the sterilization process. According to yet other embodiments, achieving high-level disinfection of an object utilizing the sterilizer 10 can involve deactivation of a suitable portion of the biologically-active contagions to achieve at least a 1 $\log_{10}$ reduction of such contagions on the object that remain infectious (i.e., no more than $\frac{1}{10}^{th}$ of the biologically-active contagions on the object remain active or infectious at a time when the decontamination process is completed). According to yet other embodiments, achieving high-level disinfection of an object utilizing the sterilizer 10 can involve deactivation of a suitable portion of the biologically-active contagions to achieve at least a 3 $\log_{10}$ reduction (i.e., $\frac{1}{1,000}^{th}$) of such contagions on the object. According to yet other embodiments, achieving high-level disinfection of an object utilizing the sterilizer 10 can involve deactivation of a suitable portion of the biologically-active contagions to achieve at least a 5 $\log_{10}$ reduction (i.e., $\frac{1}{100,000}^{th}$) of such contagions on the object.

Similarly, sterilization of an object utilizing the sterilizer 10 can involve deactivation of a suitable portion of the biologically-active contagions to achieve at least a 6 $\log_{10}$ reduction (i.e., $\frac{1}{1,000,000}^{th}$) of such contagions on the object. Yet other embodiments requiring sterilization of the object can result in a complete and total absence of viable organisms on the object at a time when the decontamination process is completed.

Thus, although referred to as a "sterilizer" 10 herein for convenience, it is to be understood that the sterilizer 10 subjects objects to a decontamination process that at least disinfects, and optionally sterilizes, the objects by exposing the objects to a disinfectant, interchangeably referred to herein as a sterilizing agent, to deactivate (e.g., kill or otherwise render no longer infectious) a portion of a biologically-active contaminate present on the objects. Once the decontamination process is complete, the objects are suitable for use in a sterile field such as an operating room during a surgical procedure or other healthcare-related practice.

Subjecting a label 12 to a decontamination process utilizing the sterilizer 10 substantially sterilizes the label 12, on demand, to render the label 12 substantially sterile, and suitable for use in a healthcare, medical or life science application (referred to generally herein as a "medical application"), at a time when the label 12 is to be applied to an object and used for labeling purposes in the medical application. For instance, the label 12 can identify a medicinal substance in a vial or syringe, for example, to be administered to a patient, labeling a medical device used in the medical application performed at a healthcare facility, labeling any other object encountered in the medical application, and the like. However, for the sake of brevity, the embodiment of the sterilizer 10 and the sterilization process for decontaminating the label 12 is described as disinfecting the label 12 for labeling a medicinal substance such as a medication to be administered to a patient. Further, the label 12 includes label content 14 printed thereon, and the label content includes a barcode 16 or other machine-readable code encoding at least a portion of the label content represented using human-readable characters that are readable with the human eye, and without the assistance of a computer.

For the embodiment shown in FIG. 1, the sterilizer 10 includes a cabinet 18 or housing that houses components operable to expose the label 12 to a sterilizing agent and substantially sterilize the label 12. Internal components of the sterilizer are shown in, and described with reference to FIG. 3. The cabinet 18 includes an inlet aperture 20 through which the label 12 enters a disinfection chamber 21 (FIG. 3) within an interior of the cabinet 18, where the label 12 is exposed to the sterilizing agent. The sterilizing agent can be any substance, form of energy, or other agent that kills a substantial portion of any living organisms on the surface of the label 12 to render the label 12 substantially sterile. Examples of suitable sterilizing agents include, but are not limited to UV light, liquid or dry chemical disinfectants, steam, radiation, etc. . . . For the sake of brevity, however, the sterilizing agent is described herein as UV light.

The cabinet 18 can optionally be adapted to cooperate with a label printer that receives control signals transmitted by a computer processor to apply machine-printed (as opposed to hand written) label content onto the label 12. For such an embodiment, the inlet aperture 20 is arranged to receive the label 12, optionally after the label content has been applied to the label 12 and the label 12 has been deposited into the sleeve 24, output from the label printer without human intervention. Thus, labels 12 with machine-printed label content can be subjected to the decontamination process and placed in a condition suitable for use in the medical application as part of the same operation.

Substantially-sterile labels 12 exiting the cabinet 18 after being exposed to the sterilizing agent, referred to generally as "sterile labels 12" and shown in FIG. 1 in broken lines, exit an outlet 29 (FIG. 3) and are received and collected by a bin 22, from where the sterile labels 12 can be retrieved for use in the medical application.

The label 12 in FIG. 1 is placed within a sleeve 24 that is substantially transparent to the UV light used as the sterilizing agent. Embodiments of the sleeve 24 can include an adhesive that secures portions of the material forming the sleeve 24 to itself, thereby forming a pocket that is closed on three sides as shown in FIG. 1. To remove the sterile label 12 following completion of the disinfection process, a user can grasp opposite sides of the material forming the sleeve 24 at the open end 26 and pull the opposite sides apart. This causes the material of the sleeve to separate along the longitudinal edges of the sleeve (i.e., the sides of the sleeve 24 leading to the open end 26) to expose the sterile label 12 for removal from the sleeve 24.

The label 12 can optionally be placed within the sleeve 24 adhered to the stock release liner on which the label 12 is acquired from the manufacturer. For use in a medical application, the stock release liner and/or the label 12 can optionally be subjected to a decontamination process and packaged in a sterilized condition before being transported to the end user. Since the surface of the label 12 with a pressure-sensitive adhesive that cooperates with the stock release liner is not exposed to the ambient environment before the label 12 is peeled from the stock release liner, that portion of the label 12 remains in a substantially decontaminated state even if the UV light emitted by the sterilizer 10 does not penetrate the stock release liner and reach that surface of the label 12.

According to alternate embodiments, labels 12 that are not subjected to a decontamination process before being transported to the end user can be removed from the stock release liner on which the label 12 was acquired before being subjected to the decontamination process performed by the sterilizer 10. The label 12 removed from the stock release liner can be applied to a release surface of a substrate that acts as a sterilizing carrier and supports the label 12 while it is exposed to the sterilizing agent within the decontamination chamber 21. The release surface of the sterilizing carrier allows the label 12 to be releasably adhered to the sterilizing carrier and subsequently removed without significantly degrading the adhesiveness of the pressure-sensitive adhesive applied to the surface of the label 12. The sterilizing carrier can optionally be formed from a material that is substantially-transparent to UVC or other light used as the sterilizing agent. Thus, during the sterilization process described herein both major, planar surfaces of the label 12 (i.e., the surface bearing the label content and the opposite surface provided with the adhesive) can be exposed, optionally concurrently or at least during the same pass through the disinfection chamber 21, to the UVC or other light or energy used as the sterilizing agent.

Regardless of the carrier on which the label is supported, the label 12 can be introduced to the sterilizer 10 on its own, as a separate object that is separable from (e.g., removable from the sterilizer 10 to be used in the medical application) the sterilizer 10. The label 12 is separable from the sterilizer 10, and is introduced through the inlet aperture 20 and is removed from the sterilizer 10 upon exiting through the outlet aperture 29. Thus, the label 12 in the sleeve 24 can be transported through the sterilizer 10 by rotation of the rollers 30 as described below rather than resting on a conveyor belt or other such transport surface, for example. Transporting the label 12 within the sleeve 24 without placing the label 12 onto a conveyor belt or other carrier while the label 12 is exposed to the sterilizing agent in the decontamination chamber 21 allows both major planar surfaces of the label 12 to be concurrently exposed to the UVC light or other sterilizing agent. The major planar surface that would be shielded from the UVC light when resting on a conveyor belt while exposed to the light(s) 38 is instead exposed to the UVC light from the light(s) 38 as described below. Once the decontamination process is complete and the sterile label 12 exits the outlet aperture 29, the sterile label 12 is removed from the sterilizer 10 to be used for labeling an object or substance in the medical application.

The sleeve 24 includes an open end 26 through which the label 12 is introduced to an interior of the sleeve 24. The open end 26 can optionally lack a sealing mechanism, to remain open throughout the sterilization process performed by the sterilizer 10. For example, the sleeve 24 can be made of substantially-transparent polypropylene or other suitable material of suitable thickness to permit transmission of a substantial portion (e.g., at least 60%, or at least 80%, or at least 90%, or at least 95%) of the UV light emitted by the sterilizer 10. According to one embodiment, the material forming the sleeve 24 can optionally be approximately 1.6 mils. (i.e., 0.001 in.) thick, and optionally be formed by joining two single sheets of material along a plurality (i.e., three) of the sides, but left separate at the open end 26.

The sleeve can have any desired dimensions, and can optionally be sized to include an air space 28 separating the open end 26 from the portion of the label 12 closest to the open end 26 while the label 12 is fully inserted into the sleeve 24. The air space 28 can serve as a temporary sterility barrier that separates the closest portion of the label 12 from the ambient environment of the sterilizer 10, thereby interfering with the introduction of contagions to the label 12 within the sleeve 24 while the sleeve is being transported from the bin 22 to the sterile field for use. As described in detail below, the label 12 remains in the sleeve 24 following the sterilization process for only a limited length of time before being used in the medical application, and the size of the air space 28 can be suitable for interfering with the introduction of contagions during that limited time period. For example, air space 28 can include a distance Y separating the closest portion of the label 12 from the open end 26 of at least one (1 in.) inch when the label 12 is fully inserted into the sleeve 24.

Figure 2:
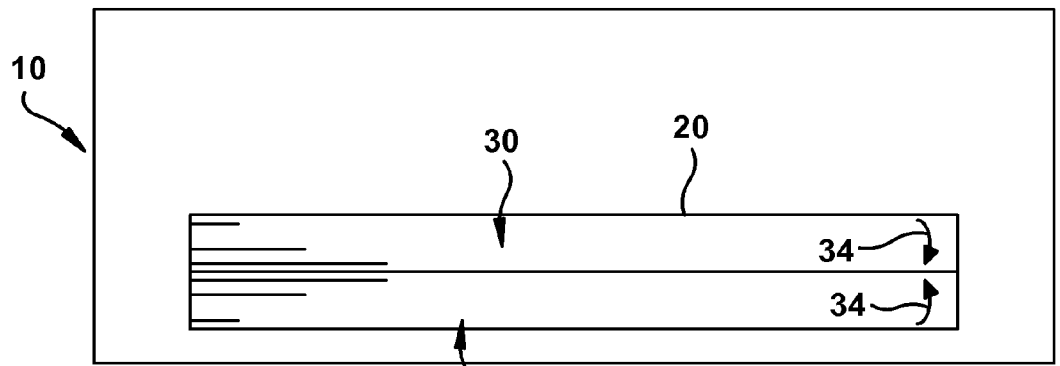
FIG. 2 shows a view into an illustrative embodiment of an inlet aperture of a sterilizer, where a peripheral surface of opposing rollers abut against each other to interfere with the transmission of light from within the sterilizer into an ambient environment.

FIG. 2 provides a view into the inlet aperture 20 of the sterilizer 10 showing an illustrative arrangement of a plurality or rollers 30 that can collectively act as a feeder that transports the label 12 within the cabinet 18 and controls the duration of the exposure of the label 12 to the sterilizing agent. As shown, a peripheral surface 32 (FIG. 3) of one roller 30 abuts against a peripheral surface 32 of an opposing roller 30 adjacent to the aperture 20. The peripheral surfaces 32 of one or each of the plurality of rollers 30 can be formed from a substantially-elastically-compressible material, such as a polymeric material for example. Contact between the peripheral surfaces 32 of the rollers 30 causes elastic deformation of those peripheral surfaces 32. This deformation of the peripheral surfaces 32 abutting against each other establishes a "light seal" that blocks at least a portion, or optionally substantially all of the UV light that would otherwise be transmitted between the rollers 30, if separated from each other, and escape the cabinet 18 through the aperture 20. The rollers 30 are counter rotating in the directions shown by arrows 34 in FIGS. 2 and 3. According to alternate embodiments, the rollers can optionally be formed from inelastic materials such as a metal or metal alloy that are UVC resistant, for example, or can otherwise tolerate prolonged exposure to the sterilizing agent employed. One, or optionally each such roller can optionally be adjustably mounted in such a manner as to allow an optimally small aperture to be created there between, allowing a greater friction fit between the rollers while still obtaining the required "light seal" through appropriate geometric component alignment. For example, one or each roller can be movably mounted and urged generally toward the other roller, thereby receiving the label 12 in the sleeve 24 between the rollers with enough friction to allow rotation of the rollers 30 to control transportation of the sleeve 24 containing the label 12 into the disinfection chamber 21 as described herein.

Figure 3:
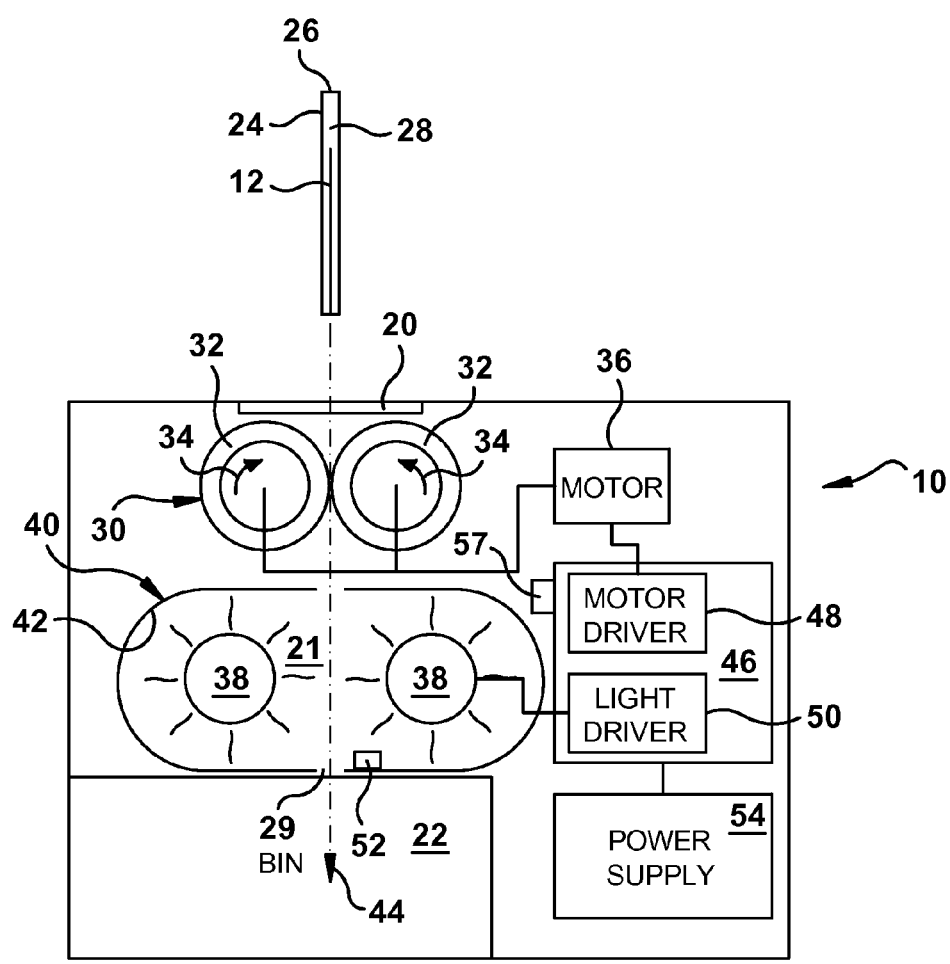
FIG. 3 shows a side view, partially cutaway, of an illustrative embodiment of a sterilizer for performing a sterilization process, on demand, on a label bearing computer-printed label content to substantially-sterilize the label.

FIG. 3 shows a partially cutaway view of an illustrative embodiment of a sterilizer 10 for subjecting a label 12 to a sterilization process that, when performed, substantially sterilizes the label 12, on demand, to render the label 12 substantially sterile, and suitable for use in the medical application. As shown in FIG. 3, the sterilizer 10 includes counter-rotating rollers 30 driven by an electric motor 36 or other prime mover. The peripheral surfaces 32 of the rollers 30 receive and engage the sleeve 24 containing the label(s) 12 to be sterilized by the sterilizing agent. Rotation of the rollers 30 feeds the sleeve 24 containing the label 12 into the disinfection chamber 21, where the label 12 in the sleeve 14 is exposed to UVC light emitted by spaced-apart UVC lights 38, for example, that emit UVC light as the sterilizing agent. When the open end 26 of the sleeve 24, which is introduced via the aperture 20 with the open end 26 in an upward orientation as shown in FIGS. 1 and 3, is disengaged from the rollers 30, the sleeve with the label(s) 12 is deposited into the bin 22. Although such a vertical orientation of the sterilizer 10 allows sterilized labels 12 to fall into the bin 22 under the force of gravity, other embodiments of the sterilizer 10 can include a horizontal orientation, or other orientation, where the labels 12 are transported in a plane without gravity assistance.

For the embodiment in FIG. 3, the sterilizer 10 includes at least one, and typically a plurality of, UVC lights 38 for applying a desired dose of UVC light to the sleeve 24 and the label 12 contained within the sleeve 24. As mentioned above, the material forming the sleeve 24 is generally transparent to UVC light such that the label(s) 12 contained within the sleeve 24 receive the UVC light substantially un-attenuated, as emitted from the light(s) 38. At least one light 38 can be arranged on each, opposite side of the major surfaces of the labels 12 as they pass through the disinfection chamber 21 to emit UVC light that impinges the opposite, major surfaces of the labels 12 concurrently. The sterilizer 10 can be adapted to support any size of sleeve and label combination. The lights 38 can be positioned within the sterilizer 10 such that the sleeve 24 passes within approximately one half (0.5 in.) inch of at least one, and optionally both lights 38, or within approximately one quarter (0.25 in.) inch of at least one, and optionally both lights 38, at the sleeve's closest point relative to the light(s) 38. In other words, a distance separating the sleeve 24 from one or both lights 38 (for an opposing pair of lights 38), taken along an axis perpendicular to the sleeve 24, is less than one half (0.5 in.) inch, and optionally less than one quarter (0.25 in.) inch.

An illustrative embodiment of the light 38 is a single, twin-tube, germicidal UVC lamp having a generally "U" shape, including two parallel tubes connected at one end by a hollow tube representing the cross member of the U shape. Such a light 38 can be installed at a suitable position to allow the label 12 or other object being decontaminated to pass between the two parallel tubes. For such an embodiment, portions of both opposite, major sides of the label 12, while unsupported by a conveyor belt or other such transporter can be irradiated with UVC light concurrently. But regardless of the configuration of the light(s) 38, the entire circumference of a portion of the object being subjected to the decontamination process can be exposed concurrently to the UVC light or other sterilizing agent. In other words, a ring-shaped region extending transversely about the entire circumference of the object is exposed to the UVC light at the same time, without being shaded by a structure transporting the object or light(s) 38.

A shield 40 including a reflective surface 42 facing an interior of the disinfection chamber 21 can be positioned adjacent to one or more of the UVC lights 38. The reflective surface 42 reflects at least a portion of the UVC light from the plurality of UVC lights 38 in a direction substantially toward a path 44 along which the sleeve 24 containing the label 12 travels from the rollers 30 to the bin 22. For example, the reflective surface 42 can reflect the portion of the UVC light generally toward at least one of the opposite major faces of the label 12 within the sleeve 24 traveling along the path 44 between the lights 38.

According to other embodiments, an inward facing surface of the shield 42 directly exposed to the UVC light can optionally be provided with, or formed from a non-reflective material, or optionally a UVC absorbing material. For instance, the inward facing surface 42 of the shield 40 can be provided with a matte black finish. The non-reflective material or UVC absorbing material can promote containment of the UVC light within the disinfection chamber 21, thereby further interfering with UVC light escaping the sterilizer 10 into an ambient environment of the user.

The position of the light(s) 38 relative to the rollers 30 also helps to prevent some of the UVC light from escaping the sterilizer 10 through the inlet aperture 20. As shown in FIG. 3 (as well as FIGS. 7, 10, 17A and 17B), each light 38 is offset relative to the rollers 30 to be spaced further away from the path 44 traveled by the label 12 or other object through the sterilization chamber 21. A distance normal to the path 44 that separates the closest portion of the peripheral surface 32 of each roller 30 from the path 44 is greater than a distance normal to the path 44 that separates the closest portion of each light 38 from the path 44. This offset allows the rollers 30 or other portion of the sterilizer 10 to obscure a direct line of sight to the lights 38 through the inlet aperture 20.

The sterilizer 10 can be deployed at a healthcare facility such as a hospital or surgical center, or anywhere a substantially-sterile label 12 is desired to label an object or substance with minimal risk of infection to a patient, for example. An operating room, treatment room, or other substantially-sterile environment can have a sterilizer 10 located inside or immediately adjacent to a substantially-sterile environment where treatment of the patient is to occur. According to such embodiments, the label 12 can optionally be generated as described in detail below within, or at least within a close proximity to the substantially-sterile environment, or elsewhere in the facility where the sterile label 12 is to be used. The sterilizer 10 can be positioned at a location where the sterile label 12 can be retrieved from the bin 22 and transported in the sleeve 24 to the substantially-sterile location where the sterile label 12 is to be used without introducing significant levels of infectious organisms.

The embodiment of the sterilizer 10 shown in FIG. 3 is an after-market peripheral that can be a stand-alone sterilization terminal to which printed labels 12 are hand fed, or an after-market peripheral to be operatively coupled to a label printer to receive printed labels 12 without requiring human transportation of the printed label 12 from the printer to the sterilizer 10. According to other embodiments, the sterilizer 10 may be provided as an integrated portion of a computerized label printer device, where the output of the label printer device may become the entry point to the sterilizer 10. In other words, for embodiments of the sterilizer 10 that cooperate with, or are integrally formed as part of the computerized label printer, the printed labels 12 output by the label printer are introduced to the sterilizer 10 to be subjected to the sterilization process before being made accessible to a user.

A controller 46 is also housed within the cabinet 18 as shown in FIG. 3. The controller 46 can optionally include a microprocessor or other computer processor programmed with computer-executable instructions, an application-specific integrated circuit "ASIC"), field programmable gate array, or any other suitable computer and/or electronic hardware and optionally computer-executable instructions stored in a non-transitory, computer-readable medium.

Regardless of its configuration, the controller 46 includes a motor controller component 48 that is adapted to control an angular velocity at which the roller(s) 30 rotate. The angular velocity can be established by the motor controller component 48 independent of any specific type of infectious organism to be deactivated or otherwise protected against. According to such embodiments, the operational state of the light(s) 38 can be maintained (i.e., no automated adjustments to the light output by the controller 46) and the angular velocity of the rollers 30 adjusted based on the output of the light(s) 38 sensed by a suitable sensor 52 described in detail below. Further, the light(s) 38 can be operated during use at or near their optimum or maximum output, or at least an output substantially greater than that required to kill event the most UVC resistant infectious organisms reasonably expected to be encountered by the sterilizer 10 when used as intended, whenever the lights 38 are on. In other words, the motor controller component 48 can control the angular velocity of the roller(s) 30 based on a control algorithm that optionally excludes from consideration a specific infectious organism(s) sought to be deactivated.

Alternate embodiments of the motor controller component 48 can optionally include pulse-width modulation ("PWM") control circuitry and/or computer-executable instructions, a stepper motor controller, or any other suitable control components to vary the angular velocity of at least one, and optionally each of the rollers 30 as described herein. An optional proximity sensor can be provided to the sterilizer 10 to sense the presence of an object adjacent to the aperture 20 where the label 12 in the sleeve 24 is introduced to the sterilizer 10. Such a proximity sensor is operatively connected to the controller 46 to transmit a signal that causes the motor driver 48 to initiate operation of the rollers 30 and thereby transport the label 12 in the sleeve 24 into the interior of the sterilizer 10 in response to the sleeve 24 with the label 12 being placed in close proximity to the aperture 20. Accordingly, operation of the sterilizer 10 can be automatic, and responsive to introduction of the label 12 to the sterilizer 10 instead of requiring manual input of operational commands to perform a sterilization process.

Yet other embodiments can include establishing a generally fixed angular velocity of the rollers 30 that is suitable to ensure at least a minimum, threshold exposure of the object to the sterilizing agent during the decontamination process. For instance, the fixed angular velocity can be established based on a worst-case scenario of the strength of the sterilizing agent utilized to deactivate the most resilient living organisms known. Accounting for any degradation of the sterilizing agent over time (e.g., assuming an accelerated 50% degradation of light intensity of a UVC light 38), the fixed angular velocity can be established to expose the object being subjected to the decontamination process to the sterilizing agent for a period of time that is X % longer than required to kill or otherwise deactivate the most resilient known infectious organism that can reasonably expected to be encountered. The value of X can be any number greater than or equal to 20, greater than or equal to 25, greater than or equal to 30, greater than or equal to 40, or greater than or equal to 50. According to alternate embodiments, the fixed angular velocity can be established to achieve at least a minimum sterilizing factor (SF) required to effectively disinfect or sterilize an object as described in detail below.

For embodiments employing one or a plurality of UVC lights 38 to emit UVC light as the sterilizing agent, the quantity, intensity or both of UVC light emitted by the UVC lights 38 can degrade over time. An optical sensor 52 or other suitable device can optionally be provided within the cabinet 18 for sensing the intensity, power output, or other property of the UVC light emitted by the light(s) 38 indicative of the sterilization effectiveness of the UVC lights 38. The optical sensor 52 can be positioned at any suitable location where it is to be exposed to the UVC light transmitted by the UVC lights 38, such as adjacent to the path 44 along which the sleeve 24 containing the label 12 travels, a location where a portion of the light reflected by the reflective surface 42 impinges on the optical sensor 52, or the like.

The controller 46 can optionally receive a signal indicative of a value of the property sensed by the optical sensor 52. Based on this signal the controller 46, more specifically the motor controller component 48, can adjust the angular velocity of the roller(s) 30 or other property affecting the feed rate of the sleeve 24 and label 12 through the region where the UVC light sterilizes the sleeve 24 and label 12. Accordingly, the feed rate of the sleeve 24 with the label 12 can be varied, and optionally infinitely varied in an analog manner, as a function of the effectiveness of the UVC lights 38 to sterilize the sleeve 24 and label 12. The lower the sterilization effectiveness of the UVC lights 38 the slower the feed rate of the sleeve 24 and label 12 will be established by the motor driver 48.

According to a specific example, the controller 46 is operable to ensure that the sleeve 24 and its contained label 12 will always receive at least a known minimum amount of UVC intensity for at least a known minimum amount of time. Pathogens are deactivated or mutated by intensity (I) of the UVC light multiplied by the time (T) that the sleeve 24 and label 12 are exposed to the UVC light. This product is referred to as the sterilizing factor (i.e., I*T=SF). The intensity (I) of the UVC light can be sensed by the sensor circuit 52 and transmitted to the controller 46. Based on this sensed intensity (I), the controller 46, optionally the motor controller component 48, calculates the desired feed rate of the sleeve 24 and label 12 for the sensed intensity (I) to ensure that if the UVC lights 38 have a declining output (e.g., intensity degradation) over time, there is a corresponding reduction in the feed rate of the sleeve 24 and contained label 12 to maintain a substantially-constant sterilizing factor (SF) for the sleeve 24 and label 12 being transported along the path 44. This substantially-constant sterilizing factor (SF) can be maintained above a minimum threshold required to satisfy the disinfection, sterilization, or other requirements of a sterile label 12, such as requirements mandated by the U.S. Food and Drug Administration or other body governing or establishing standards limiting the introduction of infectious organisms into a substantially-sterile medical application.

A reduction in intensity (I) in the equation means that time (T) must increase, and this increase in time is achieved by the motor controller component 48 slowing down the angular velocity of the rollers 30 by transmitting an appropriate control signal to the motor 36, power supply 54 or other feature controlling the angular velocity of the roller(s) 30. If, based on the equation to remain balanced and/or achieve at least a minimum sterilizing factor (SF), the angular velocity of the roller(s) 30 falls below a predetermined value, or the time required to achieve the minimum sterilizing factor (SF) exceeds an upper limit, the controller 46 can disable the sterilizer 10, or a portion thereof (e.g., the motor 36) to stop the rollers 30 and issue an error message to the user. Additionally, a motor operating faster than appropriate, as detected by the motor driver 48, can also create an out of balance equation or low SF and again result in the controller 46 disabling the sterilizer 10, or a portion thereof, and issuing the error message.

If the sensed value sensed by the optical sensor 52 falls below a predetermined minimum allowable value the controller 46 can transmit a signal that disables at least one feature of the sterilizer 10. For instance, the if the UVC light intensity has degraded 50% from the original light intensity emitted by new UVC lights 38, the controller 46 can optionally disable at least one of: the motor(s) 36 to prevent an object from being transported into the disinfection chamber 21, and the UVC light(s) 38. The disabled features can remain disabled until the sterilizing agent is renewed, replaced, recharged or otherwise render suitable to achieve at least a minimal required level of disinfection or sterilization as described herein.

According to alternate embodiments, the controller 46 can include a resettable timer or clock, which monitors how long a sterilizing agent that is susceptible to degradation over time is used. For example, the UVC lights 38 may have a limited usable life, and the UVC light emitted thereby degrades over time. The controller 46 can determine when the UVC lights 38 have reached the end of their useful life, including a predetermined margin of error, and transmit a signal that disables the UVC lights 38, the motor(s) 36, other features or a combination thereof to prevent continued use of the sterilizer to perform the decontamination process until the UVC lights 38 are replaced. The transmission of this signal can also issue an audible, visible or both audible and visible reminder to the user to change the UVC lights 38.

The controller 46 also includes a light driver component 50 that controls operation of the UVC lights 38. The light driver component 50 can include any suitable control components (e.g., hardware and/or computer-executable instructions) to illuminate the UVC lights 38 when appropriate, and shut the UVC lights 38 off when not in use. For example, the light driver component 50 can optionally limit activation of the UVC lights 38 to times when a sleeve 24 containing a label 12 has been introduced to the sterilizer 10 to be subjected to a sterilization process. For such embodiments, there can optionally be a sensor or other device capable of detecting the introduction of a sleeve 24 containing a label 12 to the cabinet 18 via the aperture 20. In response to detecting the sleeve 24, the light controller 50 can optionally turn the UVC lights 38 on for the sterilization process.

In operation, the light driver component 50 can maintain the light(s) 38 in an operational state once the sterilizer 10 has been activated. UVC lights 38 may require a period of time (e.g., three minutes) upon being turned on to reach their optimal intensity and power output. Once the sterilizer 10 is activated, the light driver component 50 can turn the light(s) on, and keep them on continuously during a sterilization process, and even after the sterilization process has been completed for a predetermined period of time. By continuously operating the lights 38 a strobe-light effect that can shorten the expected life of the lights 38 from the expected life of the lights 38 under steady, continuous operation can be avoided. Further, continuous exposure to the UVC lights 38 allows for sterilization of labels 12 and other objects in situ, with a single pass through the UVC light field where the label is exposed to direct emissions of the lights 38. The minimum rated power of the lights 38 can optionally be selected to achieve a sterilizing factor (SF) that is at least 20% greater than the sterilizing factor (SF) required to kill the most UVC tolerant infectious organisms that are reasonably expected to be encountered on the label 12 in a particular sterile field or in another particular field in which the sterilizer 10 is intended to be used.

If, during the predetermined period of time (e.g., thirty minutes) following completion the previous sterilization process a subsequent sterilization process is not initiated, the light driver component 50 can turn the lights 38 off.

A power supply 54 is also provided to the sterilizer 10 to supply the electric energy required for operation of the UVC lights 38, the motor 36, the controller 46 (including the motor controller component 48 and the light driver component 50), or a combination thereof. The power supply 54 can optionally include a self-contained source such as a battery, fuel cell, etc. . . . , that allows the sterilizer 10 to be portable, and readily transported to different locations where it can be used without being plugged into an AC mains wall outlet supplied by an electric utility, for example. The power supply 54 can include a power conditioning circuit that receives electric energy from a conventional wall outlet supplied by an electric utility or other external source of electric energy, and converts the received electric energy into a form and magnitude suitable for operation of the sterilizer 10.

Figure 4:
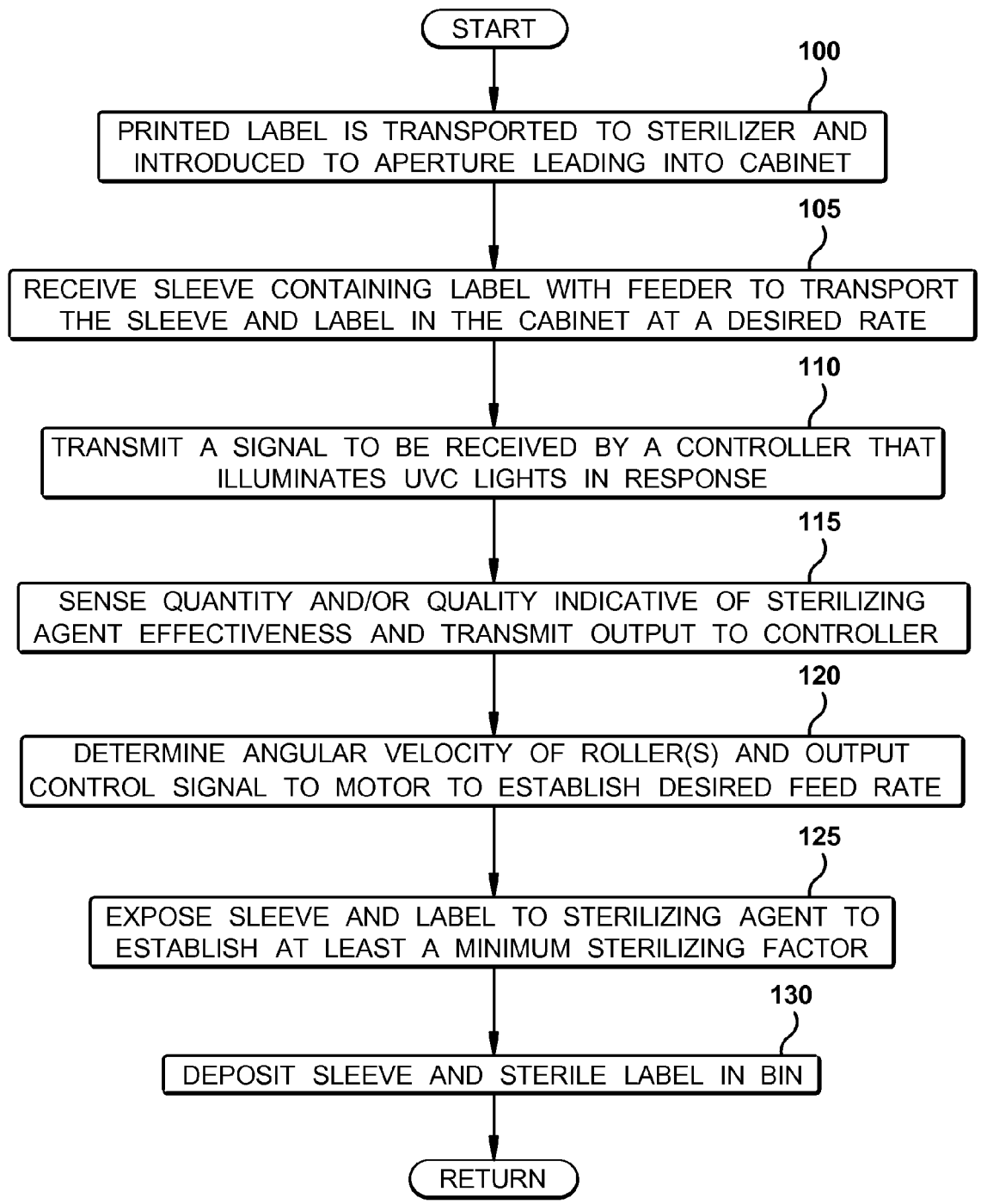
FIG. 4 shows a flow diagram graphically illustrating an embodiment of a method of substantially-sterilizing a label for use in a medical field.

An illustrative embodiment of a method of sterilizing a label is graphically depicted in FIG. 4. At step 100, a nurse, anesthesiologist, or other user can produce a label 12 by printing the desired label content using a computerized label printer at a healthcare facility, and insert the label 12 into a sleeve 24. The label 12 contained in the sleeve 24 is transported to the aperture 20 in the cabinet 18 of the sterilizer 10. Upon being introduced to the cabinet 18 via the aperture 20, a portion of the sleeve 24 is received between the counter-rotating rollers 30, which can be manually activated by the user and/or activated automatically by the controller 46 in response to receiving signal indicative of the label's presence, to thereby draw the sleeve 24 containing the label 12 into the cabinet 18 at step 105. At step 110 the light driver component 50 illuminates the UVC lights 38 of the present embodiment, to emit UVC light as the sterilizing agent.

The sensor 52 senses a quality and/or quantity indicative of the effectiveness of the UVC lights 38, and transmits an effectiveness signal that is received by the controller 46 at step 115. Based on the effectiveness signal, the motor controller component 48 determines an angular velocity of the rollers 30 suitable to establish an appropriate feed rate for the sensed effectiveness of the UVC lights 38 and outputs a control signal to control operation of the motor 36 driving the rollers 30 at step 120 to drive the roller(s) 30 at the determined angular velocity. Operating the rollers 30 at this angular velocity assures a minimum sterilizing factor (SF), above a threshold minimum value mandated for the particular medical application where the label 12 is to be used, is achieved.

At step 125, the major planar surfaces of the sleeve 24 and label 12 are exposed to the UVC light for a duration that corresponds to the feed rate established by operation of the rollers 30. The UVC lights 38 provided on opposite sides of the sleeve 24 and label 12 emit UVC light that impinges on the label 12 through the sleeve material. Such an arrangement allows for substantial sterilization of opposite sides of the sleeve 24 and label(s) 12 concurrently.

Once the sleeve 24 and sterile label 12 are deposited in the bin 22 at step 130, the sleeve 24 and sterile label 12 are retrieved and the open end 26 of the sleeve 24 torn apart once the sleeve 24 with the label 12 has been transported to the sterile environment. The sterile label 12, now removed from the sleeve 24, can be applied to the object to be labeled.

Figure 5:
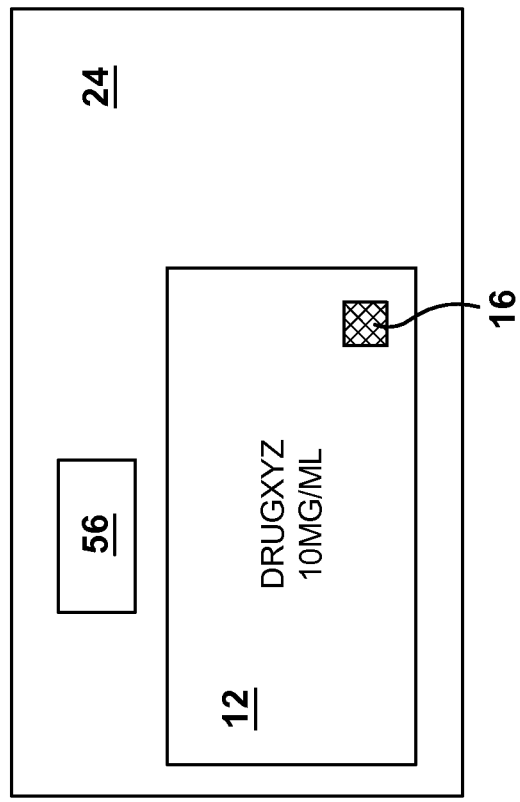
FIG. 5 shows an illustrative embodiment of a sleeve for containing a label bearing computer-printed label content during a sterilization process, the sleeve allowing handling of the label following the sterilization process without a substantial effect on the substantially-sterile condition of the label.

To provide a visual indicator whether the sterilization process performed by the sterilizer 10 has sterilized the label 12 to the desired degree (i.e., established at least the minimum sterilization factor (SF)), the sleeve can be provided with a marker 56 as shown in FIG. 5. The marker can be sensitive to the sterilizing agent employed by a given embodiment of the sterilizer 10. For the illustrative embodiment described herein using UVC lights 38 emitting UVC light as the sterilizing agent, the marker 56 can optionally be sensitive to UVC exposure. For such an embodiment, the marker 56 can include a photochromic material that has a yellow appearance to the human eye before being exposed to UVC light. The yellow appearance indicates that the sleeve 24, and accordingly, the label 12 therein, have not yet been exposed to the UVC light during a sterilization process. Upon being exposed to the UVC light as described herein during sterilization, the appearance of the marker 56 changes from yellow to a green color. The marker 56 selected can optionally require exposure to at least a threshold minimum UVC light before the transition from yellow to green can begin. Thus, when the sleeve 24 containing the label 12 is retrieved from the bin 22, a user can get an immediate visible indication that suggests whether the sleeve 24 and label 12 have been suitably exposed to the UVC light to establish at least the minimum sterilizing factor (SF). According to an embodiment of the invention, the degree of sterilization or minimum sterilizing factor (SF) can be a value established by a governing body that establishes a sterilization standard mandating a predetermined degree of sterilization for use of an object in a sterile environment, such as an operating room, where a surgical procedure is to take place.

According to alternate embodiments, the marker 56 can optionally have a limited memory, meaning that the marker 56 will retain its green color appearance for up to a maximum amount of time once exposure to the UVC light is terminated. As mentioned above, the air space 28 separating the portion of the label 12 closest to the open end 26 of the sleeve 24 serves as a sterility barrier for only a limited length of time. The marker 56 can be adapted to have a memory that is no greater than, and optionally slightly less than the limited length of time that the air space 28 can effectively serve as the sterility barrier. Thus, if the user is called away from the sterilizer 10 during the performance of a sterilization process, the user can return to the sterilizer 10 to retrieve the sterile label 12 within the sleeve 24 from the bin 22. Upon retrieving the sleeve 24 containing the label 12, the user can visually inspect the marker 56 to determine whether the sterility of the sterile label 12 has been compromised due to the passage of time. If the marker 56 is still green in appearance the user can rely on the marker 56 in concluding that the sterile label 12 still maintains at least the minimum sterilizing factor (SF) and is suitable for use in the medical application. To the contrary, if the marker 56 has a yellow appearance or any appearance other than the a green color, the user determines that the sleeve 24 containing the label 12 should be subjected to the sterilization process with the sterilizer 10 once again before utilizing the label 12 in the medical application.

The embodiment of the marker 56 described above and shown in FIG. 5 is a generally rectangular sticker adhered to an external surface of the sleeve 24. According to another embodiment shown in FIG. 8, the photochromic material included as part of the marker 56 can optionally be combined with, or provided to an adhesive that couples sides of the sleeve material together, or otherwise provided adjacent to one, a plurality, or optionally three or all sides of the sleeve 24. For embodiments where the photochromic material is provided to the adhesive, the adhesive can optionally be a releasable adhesive, allowing the sleeve 24 to be opened along a single edge like a book to facilitate insertion and removal of the label 12, by separating the two side edges 19 from each other.

At least a transverse segment 17 of the marker 56 can be provided to span substantially the entire distance across the sleeve 24 in a direction (widthwise in the embodiment of FIG. 8) that is substantially perpendicular to the direction in which the sleeve 24 is to travel through the sterilizer 10. The marker 56 can optionally extend about a plurality of the sleeve's edges, optionally all three of the closed edges, allowing the open end 26 to be free of the marker 56. The open end 26 itself could also be provided with the marker 56 according to other embodiments. Thus, if there is an obstruction, such as material on one of the lights 38 described below, the portion of the transverse segment 17 shielded from the UVC light by the obstruction will not exhibit the same reaction as the neighboring areas of the transverse segment 17 that were not shielded from the UVC light by the obstruction. For the embodiment in FIG. 8, the transverse segment 17 of the UVC-sensitive material is substantially perpendicular to the direction in which the sleeve 24 is to travel through the sterilizer 10. The transverse segment 17 is arranged along a border of the sleeve 24 at a closed end 25 opposite the open end 26 along a length of the sleeve 24. However, according to other embodiments, the transverse segment 17b (shown in broken lines in FIG. 8) can extend at an angle other than perpendicular to the direction of travel. But according to such embodiments, the transverse segment 17b still spans the entire dimension perpendicular to the direction of travel such that an obstruction of the UVC light emitted by any portion of the light(s) 38 can be visibly discerned. Under such circumstances, the user can observe the lack of a reaction of the transverse segment portion to the UVC light and determine that a portion of the label 12 within the sleeve 24 may also not have been adequately exposed to the sterilizing agent. Applying the marker 56 to the sleeve 24 and not directly to the object being sterilized eliminates the need to later remove the marker from the object, once sterilized.

Although described above as including a photochromic material, the marker 56 can include any substance that exhibits a visible reaction in response to being exposed to UVC light or the particular sterilizing agent chosen. Further, the marker material can exhibit a unidirectional, or substantially-permanent response to being exposed to the sterilizing agent (i.e., changes color but does not revert to the original color even after being removed from the sterilizing agent for a significant period of time). According to other embodiments, the marker material can eventually revert back to its original appearance (i.e., appearance prior to being exposed to the sterilizing agent) after having been removed from the sterilizing agent for a predetermined period of time during which the sterilized label 12 is suitable for use in the sterile environment.

A machine-readable code such as a barcode, code stored by a RFID tag, etc. . . . can optionally be provided to the sleeve 24 to validate a source of the sleeve 24 used with the sterilizer 10. For such embodiments, a RFID tag can be coupled to a substrate also supporting the marker 56. The marker 56 may be applied over the RFID tag to minimize the footprint of the marker/RFID tag on the sleeve and avoid potentially shading a portion of the label 12 from the UVC light. The maker/RFID tag combination can be positioned on the sleeve 24 at a location corresponding to the air space 28 to avoid shading any portion of the label 12 in the slave 24 from the UVC light. The sterilizer 10 can optionally include an antenna 57 (FIG. 3) operatively connected to communicate with the controller 46 adjacent to the path 44 that the sleeve 24 travels through the disinfection chamber 21 for interrogating the RFID tag and read the code stored by the RFID tag. The antenna transmits a signal indicative of the code to the controller 46, which interprets the code to determine whether the sleeve 24 was supplied by an authorized source, which can be a vendor of the sterilizer 10, or a third party authorized as a source of goods compatible with the sterilizer 10.

Additionally, although the sleeve 24 is described above as being sealed on three of its four edges, leaving the open end 26 open to receive the label 12, the edge seals can optionally be hermetically sealed such as when the sleeve 24 is formed from a single, uninterrupted sheet of material that is creased at the ends other than the open end 26. The edges of the sleeve 24 according to other embodiments can optionally be non-hermetically sealed. According to other embodiments, the sleeve 24 can include a flap or other cover that closes and optionally seals (possibly hermetically) the open end 26 once the label 12 has been received.

Figure 8:
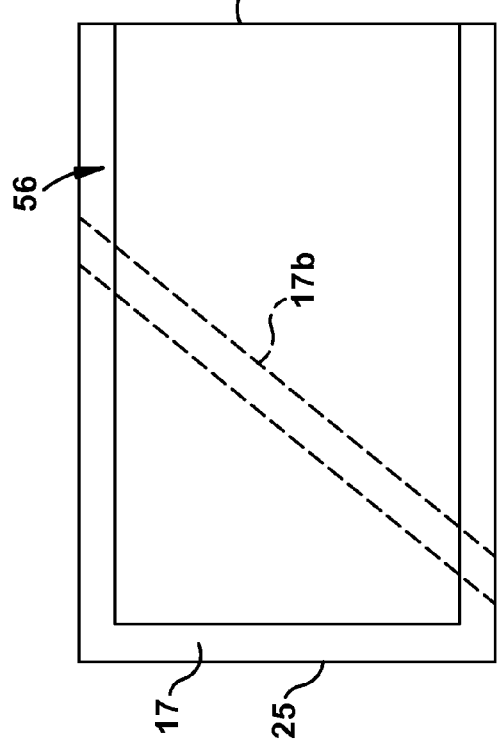
FIG. 8 shows a sleeve provided with a marker material that extends across an entire width of the sleeve.
Figure 9:
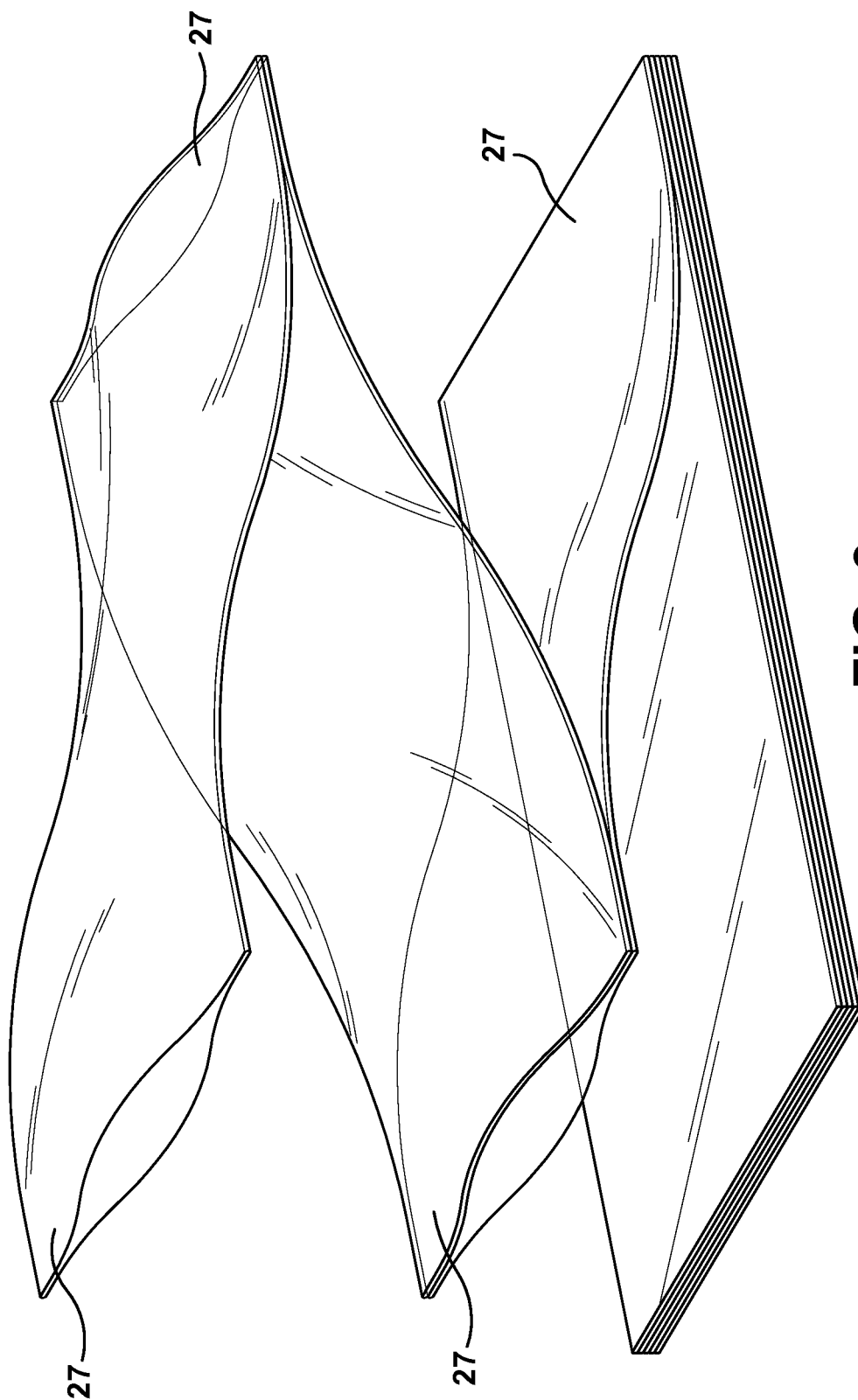
FIG. 9 shows an illustrative embodiment of an alternating stacking arrangement for sleeves to be stacked.

Single sleeves 24 are shown in FIGS. 5 and 8. However, such sleeves 24 can be supplied as a collection including a plurality of alternating sleeves 24 stacked on top of each other, in a generally z-stacked arrangement. In the z-stacked arrangement, the sleeves 24 are coupled together at alternating, opposite ends 27 by a mild adhesive as shown in FIG. 9. The mild adhesive is tacky enough to hold the sleeves 24 together, but releasable in that the sleeves 24 can be easily separated by applying a slight pulling force, by hand, on a free end of the uppermost sleeve 24.

Figure 6:
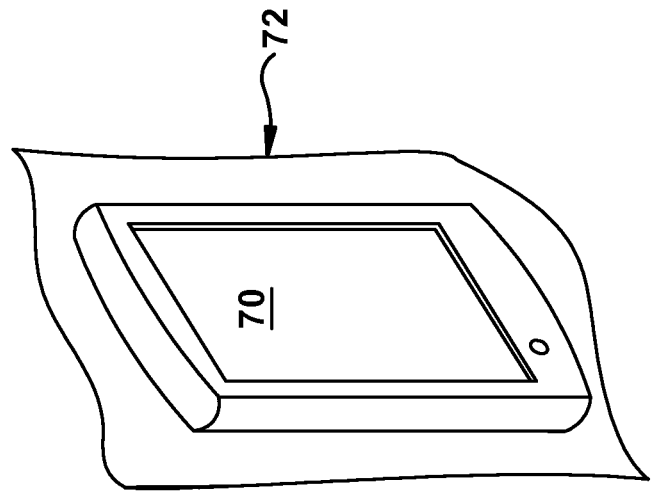
FIG. 6 shows an illustrative embodiment of a tablet computer disposed within a sleeve for sterilization.
Figure 7:
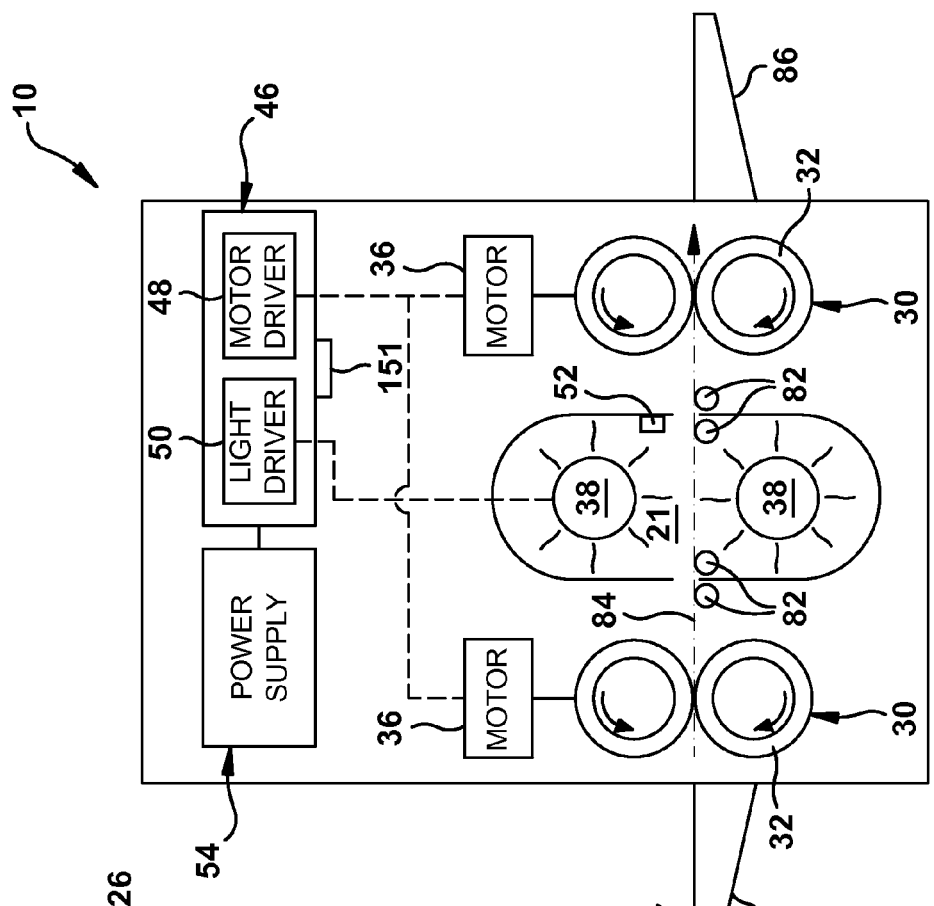
FIG. 7 shows a side, partially cutaway view of an illustrative embodiment of a sterilizer.

The embodiments of the sterilizer 10 are described above as performing a decontamination process on a label 12. However, it is to be understood that the sterilizer 10 can be adapted to perform the decontamination process on objects other than labels 12. FIG. 6 shows an illustrative embodiment of a portable electronic device in the form of a tablet computer 70 such as the ipad from Apple, Inc., for example, disposed within a sleeve 72 as another example of an object that can be subjected to the decontamination process using the sterilizer 10. Similar to the sleeve 24 described above, the sleeve 72 of the present embodiment is formed from a material that is substantially-transparent to UVC light or other sterilizing agent that penetrates the sleeve 72 to substantially sterilize the space within the sleeve 72, including the tablet computer 70. The tablet computer 70 may include recesses in its external housing, apertures, internal compartments and components, and other regions that may not be directly or otherwise exposed to the UVC light emitted by the UVC lights 38 or other sterilizing agent to achieve the desired level of disinfection, or fully sterilize the tablet computer 70. Accordingly, the sleeve 72 of the present embodiment can include a flap portion 74 (FIG. 7) or other suitable structure that can extend over an open end of the sleeve 72 through which the tablet computer 70 is inserted into the space within the sleeve 72. Thus, unlike the sleeve 24 shown in and described with reference to FIG. 1, which includes the open end 26 and relies on the air space 28 separating the label 12 within the sleeve 24 from the ambient environment, the sleeve 72 in FIGS. 6 and 7 forms a substantially air-tight enclosure around the tablet computer 70. Thus, exposing the sleeve 72 to UVC light or another sterilizing agent as shown in FIG. 7 sterilizes the exterior of the sleeve 70. And for embodiments utilizing UVC light or other sterilizing agent that can penetrate the material forming the sleeve 72 into the space within the sleeve 72, the UVC light can also substantially sterilize the space within the sleeve 72, including surfaces of the tablet computer 70 that are exposed to the UVC light or other penetrating sterilizing agent.

Figure 12:
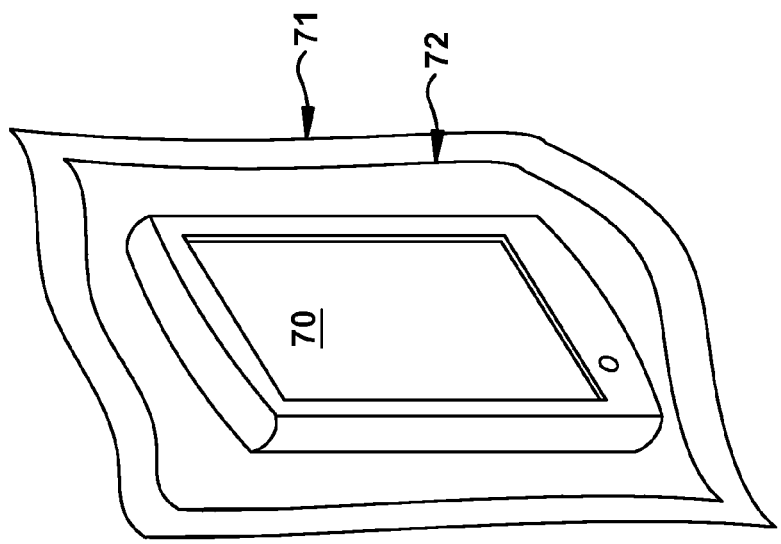
FIG. 12 shows a perspective view of a tablet computer enclosed within a plurality of sleeves.

According to an alternate embodiment, the tablet computer 70 can be inserted into a first sleeve 72, and the tablet computer 70 within the first sleeve 72 can be inserted into a second, outer sleeve 71 as shown in FIG. 12. Although each sleeve 72, 71 is illustrated in FIG. 12 as loosely enclosing the tablet computer 70 for clarity, the sleeves 72, 71 can be form fitting, meaning that they substantially conform to the dimensions of the tablet computer 70 without significant overhanging portions. Additionally, the descriptions of the marker 56, machine-readable code, and other properties of the sleeve 24 above are applicable to the sleeve(s) 72, 71 as well.

Figure 13:
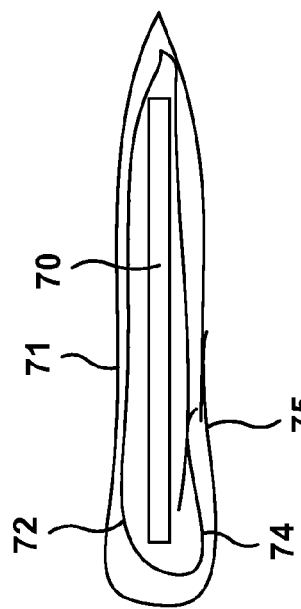
FIG. 13 shows a side view of the tablet computer enclosed within the plurality of sleeves.

As shown in the side, partially-cutaway view of the sleeves 72, 71 in FIG. 13, the flap portion 74 can be provided with an adhesive to secure the flap portion 74 to the portion of the sleeve 72 that received the tablet computer 70. The adhesive can optionally extend laterally, substantially entirely across the flap portion at a location that is to be pressed against the other portion of the sleeve 72. In this manner, the adhesive maintains the flap portion 74 in a closed state, in which it conceals an aperture 77 (FIG. 14) through which the tablet computer 70 is inserted into the sleeve 72, thereby forming the substantially air-tight enclosure around the tablet computer 70. The adhesive, like the material forming the sleeve 72 and optional flap portion 74, can be substantially transparent to UVC light, minimizing the obstruction of the UVC light impinging on the sleeve 72 from penetrating into the space within the sleeve 72.

For embodiments where the tablet computer 70 is received by the sterilizer 10 in inner and outer sleeves 72, 71, the sleeve 71 can also optionally be provided with a flap portion 75, which can optionally include an adhesive to secure the flap portion 75 to another portion of the sleeve 71, or be devoid of the flap portion 75 and/or adhesive. Thus, the flap portion 75 can be absent from the sleeve 71, or can be included with or without the adhesive, which, if included, can extend laterally, substantially entirely across the flap portion 75 at a location that is to be pressed against the other portion of the sleeve 71. In this manner, the adhesive maintains the flap portion 75 in a closed state, in which it conceals an aperture 79 (FIG. 14) through which the tablet computer 70 in the sleeve 72 is to be inserted into the sleeve 71, thereby forming the substantially air-tight enclosure around the tablet computer 70 and the sleeve 72. Again, the adhesive can be substantially transparent to UVC light, minimizing the obstruction of the UVC light impinging on the sleeve 71 from penetrating into the space within the sleeve 71.

Inserting the tablet computer 70 in the sleeve 72 into the outer sleeve 71 to be subjected to the decontamination process allows the collective unit to be retrieved from the sterilizer 10 following completion of the decontamination process and taken into the sterile environment. Once in the sterile environment, the flap portion 75 of the outer sleeve 71 can be opened to expose, and grant access to the tablet computer 70 in the sleeve 72. A recipient within the sterile environment can then reach into the outer sleeve 71 and extract the tablet computer 70 in the sleeve 72. Since the sleeves 72, 71 are substantially transparent to UVC light, the UVC light emitted by the UVC lights 38 as described herein disinfects (or optionally sterilizes) the sleeve 72 and the space within the sleeve 72 exposed to the UVC light, including portions of the tablet computer 70 disposed within the sleeve 72. In this way, the sleeve 72 is suitably disinfected or sterilized for use in the sterile environment. Most portions of the tablet computer 70 within the sleeve 72 exposed to the UVC light have also been disinfected or sterilized. And the seal between the flap portion 74 and the other portion of the sleeve 72 established by the adhesive interferes with the escape of any viable organisms remaining within the sleeve 72 that may have been shielded from the UVC light during the decontamination process.

Figure 14:
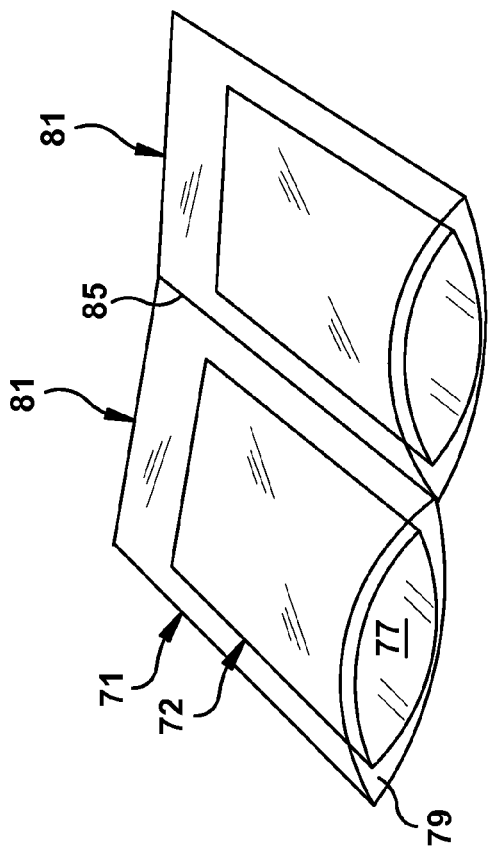
FIG. 14 shows a perspective view of a plurality of pre-assembled units of sleeves coupled together by a perforated seam.

Sleeves 72, 71 can optionally be supplied to, and received by end users in a roll or other arrangement suitable for use with a dispenser. For instance, as shown in FIG. 14, the sleeve 72 can be distributed within the outer sleeve 71 as pre-assembled unit 81. These pre-assembled units 81 can be connected to each other by a perforated seam 85, allowing the terminal pre-assembled unit 81 to be torn from the immediately adjacent pre-assembled unit 81 at the seam 85. In use, the tablet computer 70 can be inserted into the sleeve 72, optionally while the pre-assembled unit 81 being used is still coupled to the immediately adjacent pre-assembled unit 81, and the sleeve 72 sealed by closing the flap portion 74. The flap portion 75 provided to the outer sleeve 71 can be closed to seal the outer sleeve 71 and the pre-assembled unit 81 with the tablet computer 70 torn from the immediately adjacent pre-assembled unit 81 along the perforated seam 85. Aside from inserting the tablet computer 70 in the sleeve 72 into the outer sleeve 71 and subsequently removing the tablet computer 70 in the sleeve 72 from the outer sleeve 71 in the sterile environment, the description of a decontamination process performed on a tablet computer 70 in a single sleeve 72 below is also applicable to embodiments that also include the outer sleeve 71.

Referring once again to FIG. 7, the sterilizer 10 can be used to expose any object to a sterilizing agent for disinfecting or substantially sterilizing that object to an extent that renders the object suitable for use in a sterile environment such as an operating room in which a surgical procedure is to be performed on a human patient. Although shown in FIG. 7 and described below in detail as sterilizing a tablet computer 70 enclosed within a sleeve 72, the sterilizer 10 can be utilized to expose any object to be sterilized to a sterilizing agent. As shown, however, the user places the tablet computer 70 within the sleeve 72 and removes a release film that is initially protecting the adhesive provided to the flap portion 74. The flap portion 74 is folded by the user against another portion of the sleeve 72, thereby closing the aperture leading into the space within the sleeve 72 and forming the substantially air-tight enclosure around the tablet computer 70. Although the sleeve 72 is described herein as forming an enclosure that is substantially air-tight, the enclosure formed by the sleeve 72 in the closed state does not necessarily have to be air tight in the sense that it forms a hermetic seal. Rather, the sleeve 72 in the closed state should form a suitable seal that minimizes the escape of contaminates from within the sleeve 72 for a length of time required for the surgical procedure to be conducted.

Generally, the sterilizer 10 of FIG. 7 includes an inlet tray 80 on which an object such as the tablet computer 70 within the sleeve 72 can be placed and guided into the sterilizer 10. Once on the inlet tray 80, the tablet computer 70 within the sleeve 72 can be engaged by a pair of opposing rollers 30, each with a cooperating peripheral surface 32. When the tablet computer 70 within the sleeve 72 is engaged by the first pair of rollers 30 adjacent to the inlet tray 80, rotation of the rollers by the motor 36 under the control of the motor driver 48 provided to the controller 46 draws the tablet computer 70 within the sleeve 72 into the sterilizer 10. The tablet computer 70 within the sleeve 72 can be transported past a plurality of UVC lights 38, optionally including at least one UVC light 38 separate from another UVC light 38 by the table computer passing there between, at a rate based at least in part on the intensity of the lights 38 as sensed using a sensor 52. The rate can optionally also vary based at least in part on the degree of disinfection or sterilization desired. In addition to controlling operation of the motor(s) 36 driving the rollers 30, the controller 46 can also optionally control activation of the UVC lights 38 or emission of another sterilizing agent via the light driver component 50. For example, energy consumption can be minimized by energizing the UVC lights 38 only at times when the tablet computer 70 within the sleeve 72 or other object is introduced to the region where it is to be exposed to the sterilizing agent.

One or a plurality of rollers 82 or other suitable supports can optionally be provided to support the tablet computer 70 within the sleeve 72 or other object being sterilized being transported past the UVC lights 38 along the path 84. A second pair or rollers 30 can optionally be provided on a side of the UVC lights 38 opposite the first pair or rollers 30. The second pair of rollers 30 can rotate to engage the tablet computer 70 within the sleeve 72 or other object as it emerges from a space between the UVC lights 38 where the tablet computer 70 and sleeve 72 are exposed to the UVC light. The second pair of rollers 30 can then urge the tablet computer 70 within the sleeve 72 or other object out of the sterilizer 10 and onto an outlet tray 86, from where it can be retrieved in a substantially-sterile state.

Figure 10:
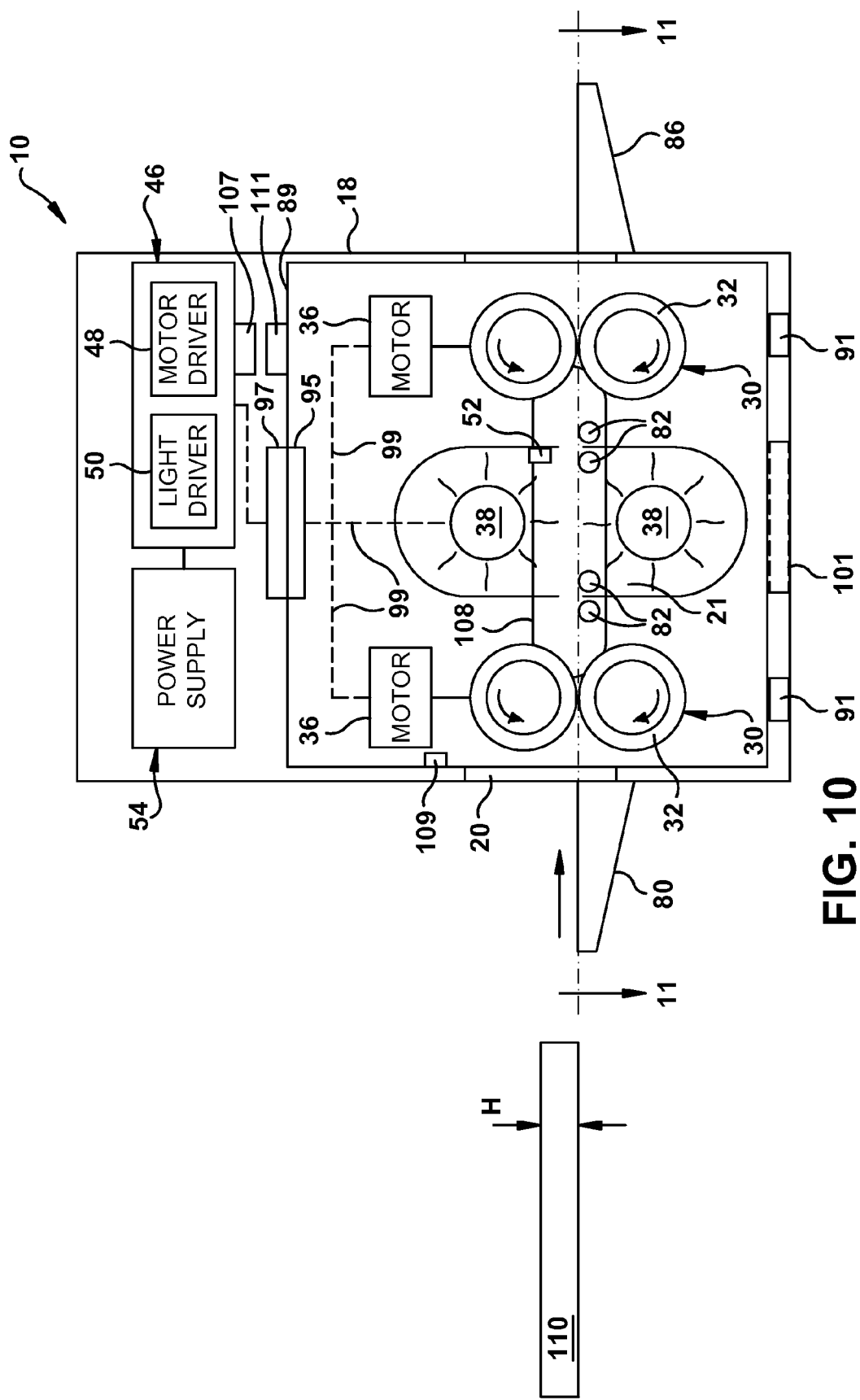
FIG. 10 shows a side, partially cutaway view of an illustrative embodiment of a sterilizer comprising a cartridge with a modular electric plug.

FIG. 10 shows another illustrative embodiment of the sterilizer 10. As shown, the lights 38, sensor 52, rollers 30 and 82, motors 36 are all included as part of a replaceable cartridge 89. The components included as part of the cartridge 89 are collectively removed and replaced together, as a singular unit. In other words, the features such as the lights 38 and rollers 52 are to be replaced together, as part of the cartridge 89 rather than separately. The cartridge 89 is modular in that it is removably coupled to the cabinet 18 by one or more, or a plurality of releasable fasteners 91, which can optionally be snap-lock, friction-fit connectors, screws, bolts and the like. The fasteners 91 can repeatedly, and without being damaged to an extent to be rendered inoperable, secure the cartridge 89 in place within the cabinet 18, release the cartridge 89 when adjusted, and secure a replacement cartridge 89 in place of the removed cartridge 89. The cartridge 89, and accordingly the lights 38, sensor 52, rollers 30 and 82, and motors 36, can be removed through an access door (not shown) provided to the cabinet 18 or otherwise removed when the cabinet 18 is partially disassembled and replaced with a replacement cartridge 89 to replace items subject to wear due to operation of the sterilizer 10 over time. Such items include at least one of: the lights 38, rollers 30 and 82, and the motors 36.

A modular connector 95 can optionally be provided at a location on the cartridge 89 to establish an interface to which a mating connector 97 can be coupled externally of the cartridge 89 to establish an electrical connection between those connectors. The connector 95 can include a pin, receptacle, or other electrical terminal can be electrically connected to internal supply lines 99 establishing a conductive pathway for supplying electric energy to each of the electrically-powered components installed as part of the cartridge 89. In the present example, the electrically-powered components can include the one or more motors 36, one or more lights 38, or a combination thereof. Further, the connector 95 can also include an electrical connection that is part of an electrically-conductive pathway along with a wire or other conductor in communication with the sensor 52 and any other such devices installed as part of the cartridge 89 to conduct control signals between the sensor 52 and other control devices installed as part of the cartridge 89 and a mating connector 97 cooperating with the connector 95. In this manner, mating the connectors 95, 97 with each other to form a single connection establishes a conductive pathway between each of the electric devices installed as part of the cartridge 89 and their respective counterparts external to the cartridge 89, such as the power supply 54 and controller 46.

According to an alternate embodiment, the mating connectors 95, 97 can optionally cooperate to form a connection 101 (shown in broken lines) at a location in the cabinet 18 that is inaccessible with human hands while the cartridge 89 is fully installed in the cabinet 18. For example, the electrical connector 97 provided to the cabinet 18 and forming a terminal connection of the electric components of the sterilizer 10 in the cabinet 18 but not installed as part of the cartridge 89 can be permanently fixed to a floor at the bottom of the cabinet 18. A spring-biased cover can be provided, and urged in a protective orientation that conceals or renders the terminals of the electrical connector 97 inaccessible without adjusting the spring-biased cover to an access orientation. A mating connector 95 can be provided at a location along a portion of the cartridge 89 that corresponds to the connector 97 on the floor. A portion of the mating connector 95 or a portion of the cartridge 89 can cooperate with the spring-biased cover to adjust the spring-biased cover to the access orientation as the cartridge 89 is installed in the cabinet 18, optionally without requiring a separate step in addition to installing the cartridge 89 to adjust the spring-biased cover. With the cartridge 89 installed, the electrical connectors 95, 97 again establish the conductive pathways, which were established without requiring the installer to manually and separately mate the connectors 95, thereby protecting the installer from being exposed to the terminals of the connectors 95, 97.

An authentication device can optionally be coupled to a portion of the cabinet 18 to confirm that the cartridge 89 installed is from an authorized source of cartridges, or at least satisfies predetermined criteria established by the original equipment manufacturer. For example, the electrical connector 97 can optionally be configured to be physically compatible with a proprietary mating connector 95, the use of which requires permission or authorization from the original equipment manufacturer. According to alternate embodiments, an RF antenna, barcode scanner, or other machine-readable code reader 107 can be provided to the cabinet 18 and operatively connected to communicate with the controller 46. The reader 107 can be situated to interrogate or otherwise interpret a badge 111 with a machine-readable code coupled to the cartridge 89. Examples of the badge 111 include a RFID tag electronically storing the machine-readable code, a label on which a barcode is printed, etc. . . . When the cartridge 89 is installed, the reader 107 can interpret the machine-readable code provided to the badge 111 and transmit a signal indicative of that machine-readable code to the controller 46. The controller 46 can execute computer-executable instructions to validate the machine-readable code as being provided to an authentic cartridge 89 from an authorized source, or transmit a warning signal in response to a determination that the cartridge 89 installed is not authentic, or has been supplied from an unauthorized source. Transmission of this warning signal can optionally result in the sterilizer 10 being at least partially, or optionally fully disabled. For instance, the controller 46 can optionally render the motor(s) 36 inoperable, thereby preventing an object from being transported into the disinfection chamber 21. According to alternate embodiments, the controller 46 can optionally prevent illumination of the light(s) 38 provided to an unauthorized cartridge 89. An audible, visible, or audible and visible alert can also optionally be issued by the sterilizer 10 in response to transmission of the warning signal to inform the user that an unauthorized cartridge 89 has been installed. Yet other embodiments of the controller 46 can include a network adaptor that facilitates communications between the controller 46 and another computer terminal over a communication network, which can be a local area network ("LAN") deployed at the healthcare facility where the sterilizer 10 is physically located, a wide area network ("WAN") such as the Internet, or a combination of a LAN and WAN.

The authentication device can also restore full operation of the sterilizer 10 in response to sensing the installation of an authorized cartridge 89 after the optical sensor 52 senses a value below a predetermined minimum allowable and disables at least one feature of the sterilizer 10 as described above. For example, a new cartridge 89 can replace an existing cartridge with UVC lights 36 that have degraded in intensity by more than 50% from the original light intensity emitted by new UVC lights 38. The authentication device can verify that the new cartridge 89 is authentic, or at least authorized for use, and enable any features disabled in response to the degradation of the UVC light intensity.

Similarly, the authentication device can reset the timer or clock provided to the controller 46 in response to sensing a new cartridge 89 has replaced an existing cartridge with UVC lights 38 that have reached the end of their useful life. The audible and/or visible reminder to the user to change the UVC lights 38 can also be withdrawn or discontinued when the timer or clock is reset.

In addition to simplifying installation, the cartridge 89 can also promote containment of UVC light, thereby limiting exposure to such a sterilizing agent to those items that are replaceable with the cartridge 89. Additionally, due to the enhanced containment afforded by the cartridge 89 a UVC light 38 that can also promote formation of ozone can be selected. The combination of ozone and high-intensity UVC light is a powerful antimicrobial, but this combination increases the wear experienced by components within the cartridge 89 compared to the wear they experience when exposed to UVC light, alone. But due to the ease with which the cartridge 89 can be replaced, this increased wear does not significantly interrupt useful operation of the sterilizer 10.

Likewise, positioning the sensor 52 within the confines of the shield 42 allows the sensor 52 to directly monitor the intensity of the lights 38 in a steady-state fashion. Such continuous feedback is communicated through the connectors 95, 97 to the controller 46 in real time. Based on the output of the sensor 52 the controller 46 can determine whether to increase or decrease the angular velocity of the rollers 30 as described in detail above by adjusting the output to the motors 36. Directly exposing the sensor 52 to the high-intensity UVC light instead of indirectly via a light pipe or reflection, for example, allows for substantially continuous (i.e., in an analog type manner instead of taking a sample once every 30 minutes or so) and accurate feedback. However directly exposing the sensor 52 to the UVC light also subjects the sensor 52 to considerable wear. But again, the sensor 52 is replaceable along with the cartridge 89 as described above, and communications between the sensor 52 and the controller 46 can be established through cooperation of the connectors 95, 97.

Figure 11:
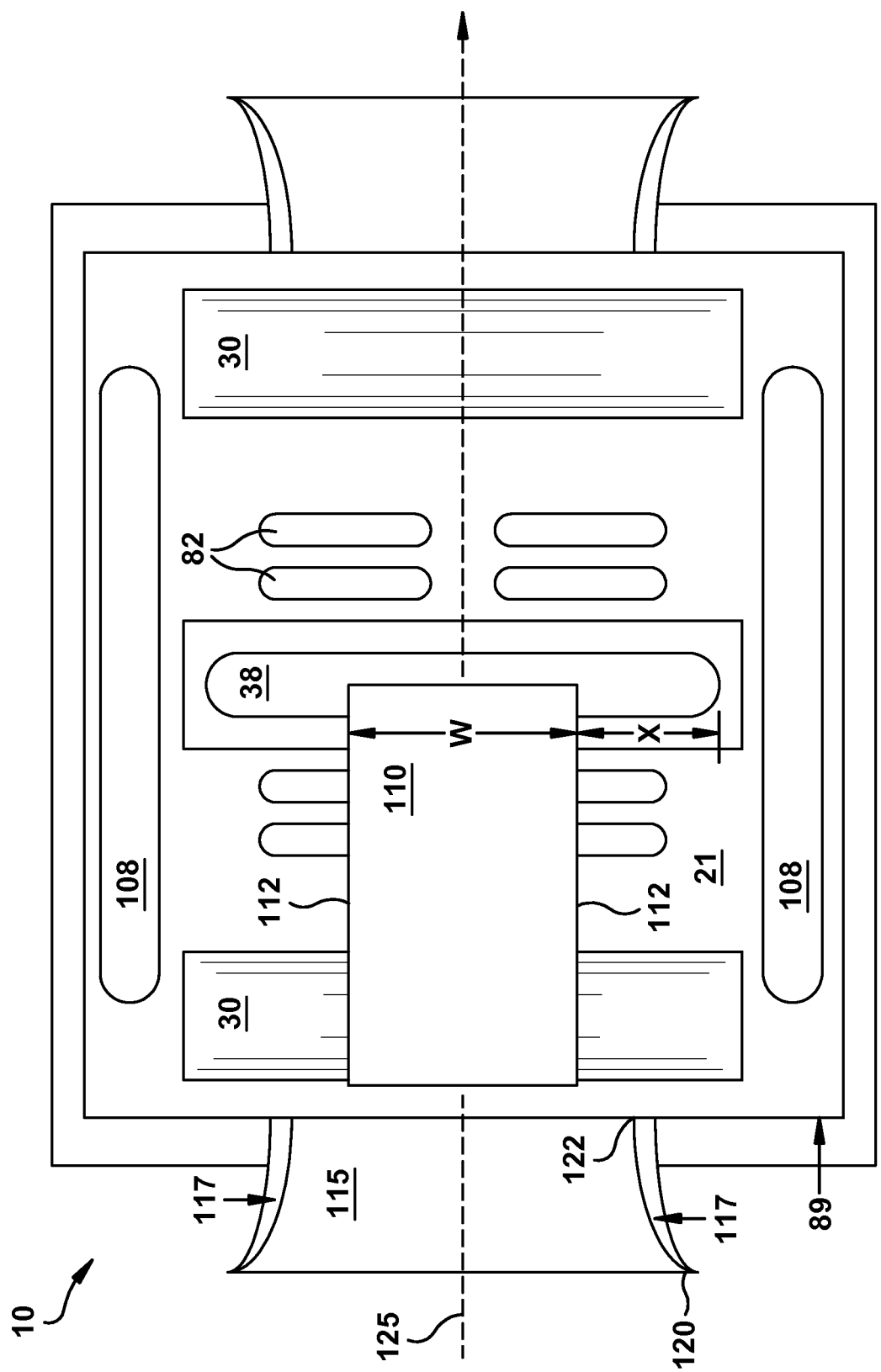
FIG. 11 shows a top, sectional view of the sterilizer shown in FIG. 10 taken alone line 11-11.

The embodiment shown in FIG. 10, and also FIG. 11, includes an optional side light 108 arranged at each opposite lateral side of the cartridge 89. The side lights 108 are also electrically connected to the connector 95 to communicate with external components such as the power supply 54 and the light driver component 50 of the controller 46 when the mating connector 97 cooperates with the connector 95.

A height sensor 109 can also optionally be installed as part of the cartridge 89. The height sensor 109 is operable to detect the height of the object, which is indicated as H in FIG. 10 as the distance the object 110 will extend between the lights 38 as it travels through the sterilizer 10. Examples of the height sensor 109 include, but are not limited to, a laser or other optical source, a capacitive device, an ultrasonic device, or any other type of contact-less sensor that can evaluate the height of an object (represented at 110 in FIGS. 10 and 11 as a tablet computer enclosed within a sleeve) entering the sterilizer 10 through the aperture 20 and transmit a signal in response indicative of the detective height. According to other embodiments, the rollers 30 adjacent to the aperture 20 where the object enters the sterilizer 10 can optionally be coupled to an adjustable suspension. An object entering the sterilizer 10 through the aperture 20 can cause the rollers 30 adjacent to the aperture 20 to be separated from each other, allowing the object to pass there between. Based on this degree of separation, a sensor monitoring the relative location of the rollers 32 transmits a signal that is conducted through the connector 95 to the controller 46.

Regardless of its configuration, the height sensor 109 can be disposed adjacent to the aperture 20 through which objects such as a tablet computer, notebook computer, and the like enter the sterilizer 10. Like the other electric components within the cartridge 89, the height sensor 109 can be wired or otherwise placed in communication with the connector 95. When the mating connector 97 is installed on the connector 95, signals transmitted by the height sensor 109 can be conducted to the controller 46 via the cooperating connectors 95, 97.

The object 110 may have a height H that is sufficiently large that the angle of incidence of the UVC light on a central region of the lateral sides 112 is great enough that the sterilizing effectiveness of that UVC light is impeded. For example, UVC light emitted by the lights 38 impinging on a central region of one lateral side 112 having an angle of incidence that is less than 60°, or optionally less than 45°, relative to that lateral side 112, requires a first exposure time during which the central region of the lateral side 112 must be exposed to the UVC light to achieve sufficient level of sterilization. The first exposure time is greater than a second exposure time required if the angle of incidence was greater than 60°, or 45°, respectively, to achieve the same level of sterilization. Accordingly, the height sensor 109 can evaluate the height H of the object 110 as it enters the sterilizer 10 and transmit a signal indicative of the sensed height H. Based on the signal transmitted by the height sensor 109, the controller 46 can determine whether the height H of the object 110 is greater than a predetermined height and, if so, slow the angular velocity of the rollers 30 to slow the rate at which the object 110 travels through the sterilizer 10, activate the sidelights 108, or a combination thereof to ensure at least a minimum sterilization factor is achieved. The adjustments made by the controller 46 can optionally be performed without adjustment to the intensity of the lights 38, and optionally without adjusting the intensity of the side lights 108 other than to activate them. Accordingly, the lateral sides 112 of tall objects 110 can also be sufficiently sterilized for use in a sterile environment.

According to an alternate embodiment shown in FIG. 11, regardless of whether the cartridge 89 includes the sidelights 108, the controller 46 can optionally adjust the angular velocity of the rollers 30; operation of the sidelights 108, if present; transmit other control signals affecting operation of the sterilizer 10, or a portion thereof, to achieve a desired sterilization factor based at least in part on a width W (FIG. 11) of the object 110 relative to a longitudinal length of the lights 38. For such embodiments, the height sensor 109 can optionally also detect a width W of the object 110 as it enters the sterilizer 10 and transmit a signal indicative of this width W to the controller 46. An arc length of the lights 38 is known to the controller 46. Such information can be stored in a computer-readable memory provided to the controller 46, for example. The controller 46 can determine, based at least in part on the signal from the height sensor 109 and the known arc length of the lights 38, whether the lights 38 extend at least a predetermined distance X beyond both lateral sides 112 of the object 110. To ensure the UVC light emitted by the lights 38 does not impinge on the lateral sides 112 of the object 110 with an angle of incidence that is less than a predetermined minimum angle, such as 45°, for example, the controller 46 can establish the predetermined distance X to be one half of the height H (X=0.5H) of the object 110.

For such an embodiment, if the lights 38 do not extend beyond each lateral side 112 of the object 110 by at least the predetermined distance X, the controller 46 can transmit a control signal to control one or more of the components within the cartridge 89 to ensure at least the minimum desired sterilization factor (SF) is achieved. For example, the control signal transmitted by the controller 46 in this instance, can result in adjustment of the angular velocity of the rollers 30 to increase the exposure time of the lateral sides 112 to the UVC light from the lights 38 during sterilization within the sterilizer 10; an operational state (e.g., turn on) the side lights 108, if present; or a combination thereof. Again, such adjustments initiated by the controller 46 can optionally be performed without adjustment to the intensity of the lights 38. In other words, the intensity of the lights 38 can be maintained substantially constant for the sterilization process even when the adjustments initiated by the controller 46 are made based at least in part on the height H, width W, or both the height H and the width W of the object 110.

If, on the other hand, the lights 38 extend more than the predetermined distance X beyond the lateral sides 112 of the object 110, the above adjustments of the angular velocity of the rollers 30, and/or the operational state of the side lights 108 to ensure sufficient sterilization of the lateral sides 112 can be omitted.

To promote consistent recognition of the objects with W and/or height H by the sensor 109, an optional guide 115 can be provided to, or coupled to the cartridge 89 adjacent to a location where the object 110 enters the cartridge 89 to be sterilized. For the example shown in FIG. 11, the guide 115 includes lateral side members 117 with a diverging entry end 120 leading to a converging exit end 122 where the object 110 enters the cartridge 89. Although shown as having diverging entry ends 120, the side members 117 can optionally be substantially planar, and arranged to be substantially parallel with a direction (indicated by arrow 125) in which the object 110 travels through the sterilizer 10. The side members 117 and can optionally be adjustable to vary the distance D separating them, and optionally mechanically or electrically linked together such that lateral adjustment of one of the side members 117 also causes adjustment of the other side member 117 to substantially centrally separate the pair along a centerline path that extends between a substantially central region of the lights 38.

The embodiments of the sterilizer 10 are described above as "pass-through" devices that perform a decontamination process on a label 12. The label 12 is introduced to the inlet aperture 20 at a first side of the cabinet 18 and exits through the outlet aperture 29 on an opposite side of the cabinet 18 for such a pass through device. The decontamination process is performed during a single, unidirectional pass of the label 12 through the disinfection chamber 21. However, it is to be understood that the sterilizer 10 can be adapted to perform the decontamination process on objects other than labels 12, and can receive and discharge the objects being disinfected or sterilized at a common side, optionally through a common aperture that functions as both the inlet and outlet aperture.

In addition to the features described above, such embodiments can involve the insertion and subsequent removal of the object into and out of the disinfection chamber 21 by transporting the object into and out of the cabinet 18, and optionally the disinfection chamber in a plurality of different directions.

FIG. 15 shows an illustrative embodiment of the sterilizer 10 having an inlet aperture 20 through which the tablet computer 70 or other object to be decontaminated is introduced to an interior of the cabinet 18 en route to the disinfection chamber 21. The embodiment appearing in FIG. 15 includes a cabinet 18 having a substantially-planar upper surface 140 on which another object such as a label printer, a computer monitor or other items commonly found in a healthcare facility where the use of disinfected or sterilized items is required. A user interface 142, shown in greater detail in FIG. 16, includes a LCD screen 144 that can visually present the user with warnings, step-by-step instructions for using the sterilizer 10, and other information concerning the sterilizer 10 and its use. An input portion 146 (FIG. 15) can include a touch-screen display, one or more buttons, or other entry devices that allow a user to input commands or other desired inputs to control operation of the sterilizer 10 as described in detail below.

Figure 17A:
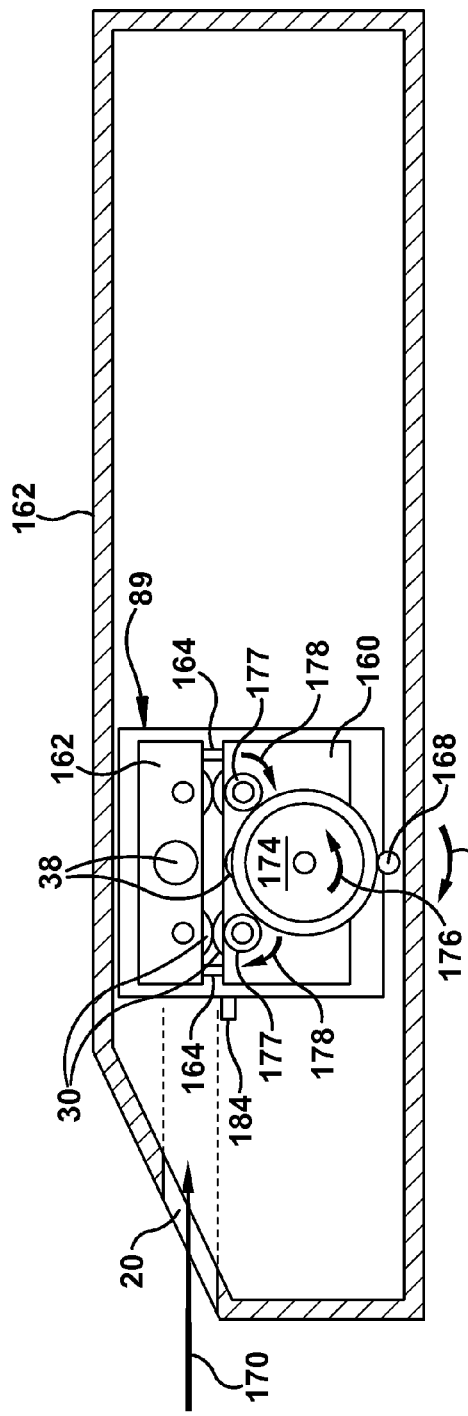
FIG. 17A shows a side, partially-cutaway view of a sterilizer with an inlet aperture through which an object is to be introduced to, and ejected from the sterilizer, and a cartridge provided to the sterilizer.
Figure 17B:
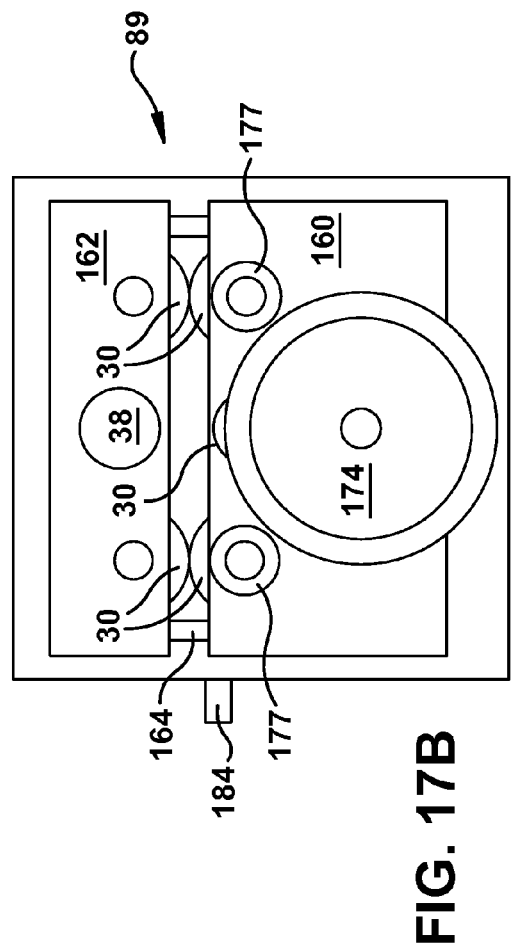
FIG. 17B shows an enlarged view of the cartridge provided to the sterilizer in FIG. 17A.

FIG. 17A shows a partially cutaway side view of the embodiment of the sterilizer 10 appearing in FIG. 15. As shown, the sterilizer 10 includes a cartridge 89 (isolated and enlarged for clarity in FIG. 17B) comprising a base portion 160 and an adjustable portion 162 that is adjustably coupled to the base portion 160 in a manner that allows a distances separating the adjustable portion 162 from the base portion 160 to be varied based on the height of an object being subjected to the decontamination process. For example, the adjustable coupling includes one or more guides 164 defining a path of adjustment of the adjustable portion 162 relative to the base portion 160. The adjustable portion 162 can be fixedly secured to the tracks 164, which are inserted into and extended from the base portion 160 during adjustment of the adjustable portion 162 relative to the base portion 160. Alternate embodiments include guides 164 that are fixedly secured to the base portion 160, allowing the adjustable portion to travel relative to the guides 164 during adjustment of the distance between the adjustable portion 162 and the base portion 160.

Each of the adjustable portion 162 and the base portion 160 supports at least one UVC light 38, and at least one, or optionally a plurality of rollers 30. As described above, the peripheral surface 32 (FIG. 3) of opposing rollers 30 provided to the base and adjustable portions 160, 162 contact each other, or are at least arranged adjacent to each other to interfere with the emission of UVC light from the cartridge 89 through the inlet aperture 20. For the embodiment appearing in FIGS. 17A and 17B, an additional set of opposing rollers 30 are provided to the base and adjustable portions 160, 162 adjacent to a distal end 166 of the cartridge 89 that is separated from the inlet aperture 20 by the UVC lights 38. The additional set of opposing rollers 30 support a leading end of the object introduced to the disinfection chamber 21 after the leading end passes beyond a plane in which the opposing UVC lights 38 are arranged.

Only the rollers 30 supported by the base portion 160 of the cartridge are actively driven by a common motor 36 (FIG. 3), which is separate from the cartridge 89, and installed as part of the cabinet 18 according to the present embodiment. Thus, when the cartridge 89 is replaced, the motor 36 remains with the cabinet 18. The rollers 30 supported by the adjustable portion 162 are allowed to rotate freely. Such rollers 30 can rotate when in contact with rotating rollers 30 supported by the base portion 160 being driven by the motor 36, or roll over a tablet computer 70 or other object entering/exiting the sterilizer 10, but are not linked to be driven by the motor 36 through a system of gears or other drivetrain. In other words, if the adjustable portion 162 is manually separated from the base portion 160 in the absence of an object entering/exiting the sterilizer 10 and the motor 36 activated, the rollers 30 supported by the base portion 160 would rotate but the rollers 30 supported by the adjustable portion 162 would not.

The motor 36, when activated under the command of the controller 46, drives a primary gear 168 shown in FIGS. 17A and 18. For instance, to transport the table computer 70 into the disinfection chamber 21, a direction generally indicated by the arrow 170, the motor 36 can cause rotation of the primary gear 168 in the direction of arrow 172 in FIG. 17A. In turn, the primary gear 168 meshes or otherwise cooperates with a drive gear 174 rotatably supported by the base portion 160 while the cartridge 89 is properly installed, causing the drive gear 174 to rotate in the direction indicated by arrow 176 in FIG. 17A. The drive gear 174 meshes or otherwise cooperates with roller gears 177 that, when rotated, cause rotation of the rollers 30 supported by the base portion 160. Since the rollers 30 supported by the base portion 160 rest against (i.e., are in contact with) the rollers 30 supported by the adjustable portion 162 in an unbiased position (e.g., the absence of an object being subjected to the decontamination process), rotation of the rollers 30 supported by the base portion 160 also causes rotation of the rollers 30 supported by the adjustable portion 162. This rotation of the drive gear 174 results in rotation of the rollers 30 in the directions indicated by arrows 178, which draws the tablet computer 70 introduced to the inlet aperture 20 into the disinfection chamber 21 in the direction indicated by the arrow 170.

Although the primary gear is shown in FIG. 17A directly cooperating with the drive gear 174, the primary gear 168 can be indirectly linked to the drive gear 174. For example, FIG. 18 shows a bottom view of the cartridge 89, with a portion of the cartridge 89 cutaway to expose components that may otherwise be partially hidden. An intermediate gear 180 is coupled to an axle 182 that, when rotated, causes rotation of drive gear 174. While the cartridge 89 of the present embodiment is fully installed the primary gear 168 driven by the motor 36 meshes or otherwise cooperates with the intermediate gear 180 to cause rotation thereof, in turn causing rotation of the drive gear 174. Use of the intermediate gear 180 offers a degree of flexibility in positioning the motor 36 and primary gear 168.

Figure 19:
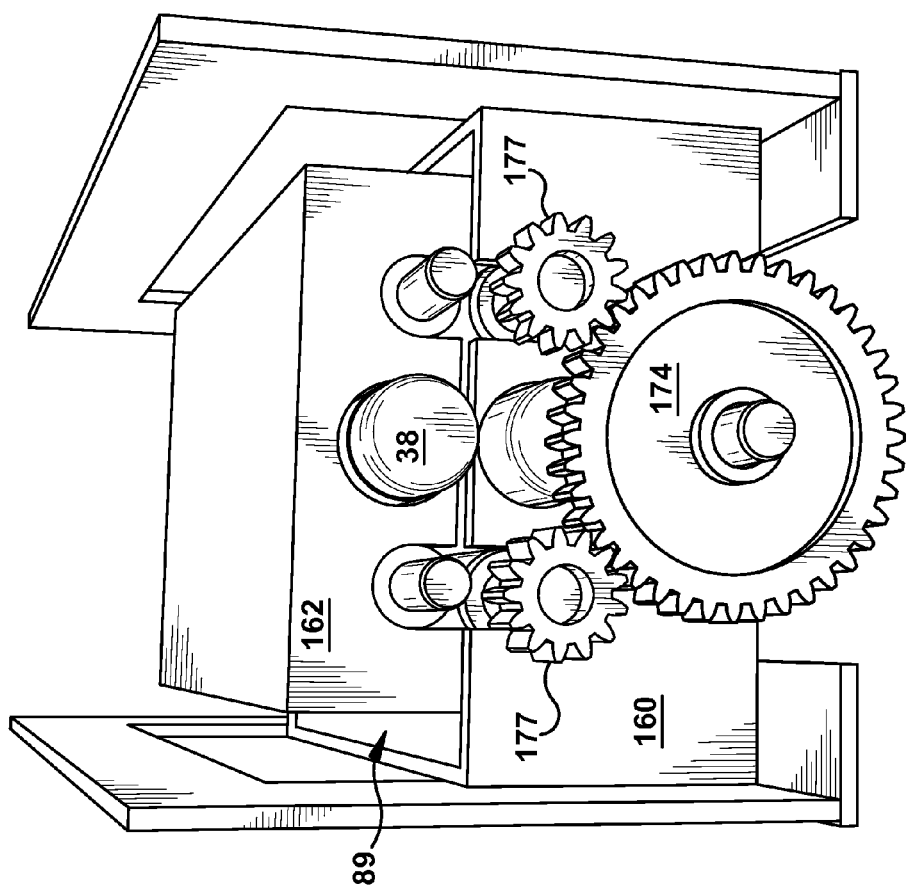
FIG. 19 shows an end view of a cartridge including an adjustable portion in an unbiased position relative to a base portion.
Figure 20:
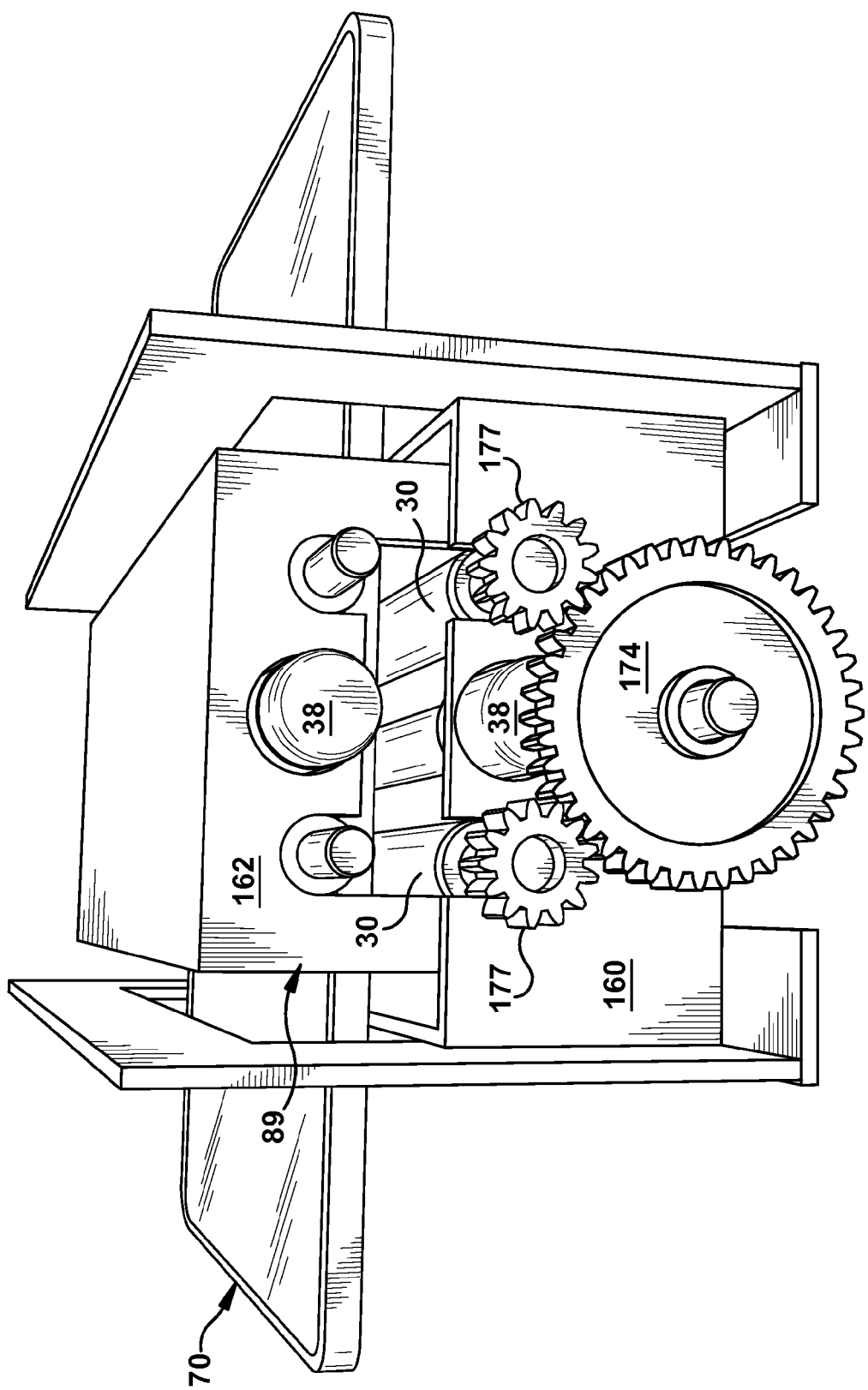
FIG. 20 shows an end view of the cartridge appearing in FIG. 19 with the adjustable portion adjusted to an elevated position relative to a base portion.

FIGS. 19 and 20 illustrate adjustment of the distance separating the base and adjustable portions 160, 162 in response to receiving the tablet computer 70. In FIG. 19, the adjustable portion 162 is in the unbiased position, where the rollers 30 supported by the adjustable portion 162 rest against the rollers 30 supported by the base portion 160. When the tablet computer 70 or other object introduced to the inlet aperture 20 is drawn into the sterilizer 10, the insertion of the tablet computer 70 or other object between the opposing rollers 30 causes the adjustable portion 162 to be elevated away from the base portion 160 by a distance approximately equal to the height of the tablet computer 70 or other object, as shown in FIG. 20. The rollers 30 supported by the adjustable portion 162 are separated from their respective opposing rollers 30 supported by the base portion 160 by the tablet computer 70. The guides 164 to which the adjustable portion 162 is secured are extended from the base portion 160 according to the illustrated embodiment. The cartridge 89 configured in this manner allows the adjustable portion 162 to be adjusted to a height that positions the UVC lights 38 in close proximity to the opposite surfaces of any object, regardless of its height, being transported between the lights 38. This close proximity can optionally be less than or equal to four (4 in.) inches separating the closest surface of the UVC lights 38 and an exposed surface of the object, less than or equal to two (2 in.) inches, less than or equal to one (1 in.) inch, less than or equal to one half (½ in.) inch, or less than or equal to one quarter (¼ in.) inch, and can be established by creating a suitable offset between the rollers 30 of each of the base and adjustable portions 160, 162 and their respective lights 38.

Operation of the motor 36 to control transportation of the tablet computer 70 during the decontamination process can be controlled based on signals received from a proximity sensor 184 (FIGS. 17A and 17B) arranged adjacent to the inlet aperture 20. When the tablet computer 70 or other object is to be introduced to the inlet aperture 20, the sterilizer 10 can be placed in an active mode (if not already in an active mode) by the manual selection of an "OK" button 154 (FIG. 16) included as part of the user interface 142. A signal received by the controller 46 in response to selection of the "OK" button 154 can illuminate the lights 38 if not already illuminated (lights 38 can be shut off after the expiration of a timeout period, but can remain on for 30 minutes or other suitable time period following a preceding use). Such a selection can also activate the motor 36 to commence rotation of the rollers 30 and indicate the beginning of a decontamination process.

The tablet computer 70 is introduced to the inlet aperture 20, where the proximity sensor 184 transmits a signal to be received by the controller 42 to indicate the presence of the tablet computer at the inlet aperture 20. With the motor 36 rotating the rollers 30, the leading end of the tablet computer 70 is received between the first set of opposing rollers 30 supported by the base and adjustable portion 160, 162. Thereby drawing the tablet computer 70 from the inlet aperture 20 into the disinfection chamber 21, where it is exposed to the UVC light emitted by the lights 38. Operation of the motor 36 in this direction continues until a communication between the proximity sensor 184 and received by the controller 46 indicates that the presence of the tablet computer 70 is no longer detected by the proximity sensor 184. A predetermined delay following receipt of such a signal can be implemented by the controller 46 based on the known location of the proximity sensor 184 and the angular velocity of the rollers 30 to ensure that the tablet computer 70 is inserted into the disinfection chamber 21 a suitable extend to expose the trailing end of the tablet computer 70 to the UVC light. Following this delay, the motor 36 can be deactivated by the controller 46, and reversed to cause the tablet computer 70 to be transported in the opposite direction, back toward the inlet aperture 20 through which the tablet computer 70 will be ejected from the sterilizer 10.

Again, the proximity sensor 184 can detect the presence of the tablet computer 70 at the inlet aperture 20 in the reverse direction and transmit a signal to be received by the controller 46. The controller 46, based on the received signal, can immediately, or following a predetermined delay, terminate operation of the motor 36 to cause only a small portion of the tablet computer 70 to appear at the inlet aperture 20. The user can then be required to manually actuate the "OK" button 154, as prompted by the LCD screen 144, to complete the decontamination process and re-activate the motor 36 to fully eject the tablet computer 70 from the sterilizer 10. Thus, the tablet computer 70 can be introduced to, and ejected from the inlet aperture 20. Following completion of the decontamination process the sterilizer 10 can be shut down by manually pressing the "STOP" button 148. Manual insertion and removal of the tablet computer 70 can be performed by inputting the appropriate instruction via the "IN" button 150 and the "OUT" button 152, respectively.

The tablet computer 70 includes a computer processor adapted to execute computer-executable instructions to communicate with the controller 46 or other portion of the sterilizer 10. For example, a tablet computer 70 in the form of an ipad can include a short-range wireless communication (e.g., Bluetooth®) antenna that can receive and transmit signals for communicating with a compatible short-range wireless communication (e.g., Bluetooth®, IEEE 802.11, etc. . . . ) antenna 151 (FIG. 7) operatively connected to communicate with the controller 46. The sterilizer 10 can optionally interface with the tablet computer 70 through the antenna 151 as part of the decontamination process. In an alternate embodiment, the tablet computer 70 may contain a sensor (e.g., a camera) that receives a signal encoding information indicative of the status of the decontamination process. For example, the signal may provide information about the length of exposure to the decontamination process.

Computer-executable instructions such as a software application, for example, can be executed by the tablet computer 70 to receive a signal transmitted by the antenna 151 or as provided by the sensor as part of the decontamination process. For example, when the user actuates the "OK" button 154 to complete the decontamination process as described above and fully eject the tablet computer 70 from the sterilizer 10, a completion signal can be transmitted by the antenna 151 as instructed by the controller 46. Alternatively, the sensor may provide a similar indication. The completion signal indicates, to the tablet computer 70, that the decontamination process performed on the tablet computer 70 has been completed. Based on receipt of the completion signal, the tablet computer 70 can exhibit a response related to the decontaminated condition thereof.

Figure 22:
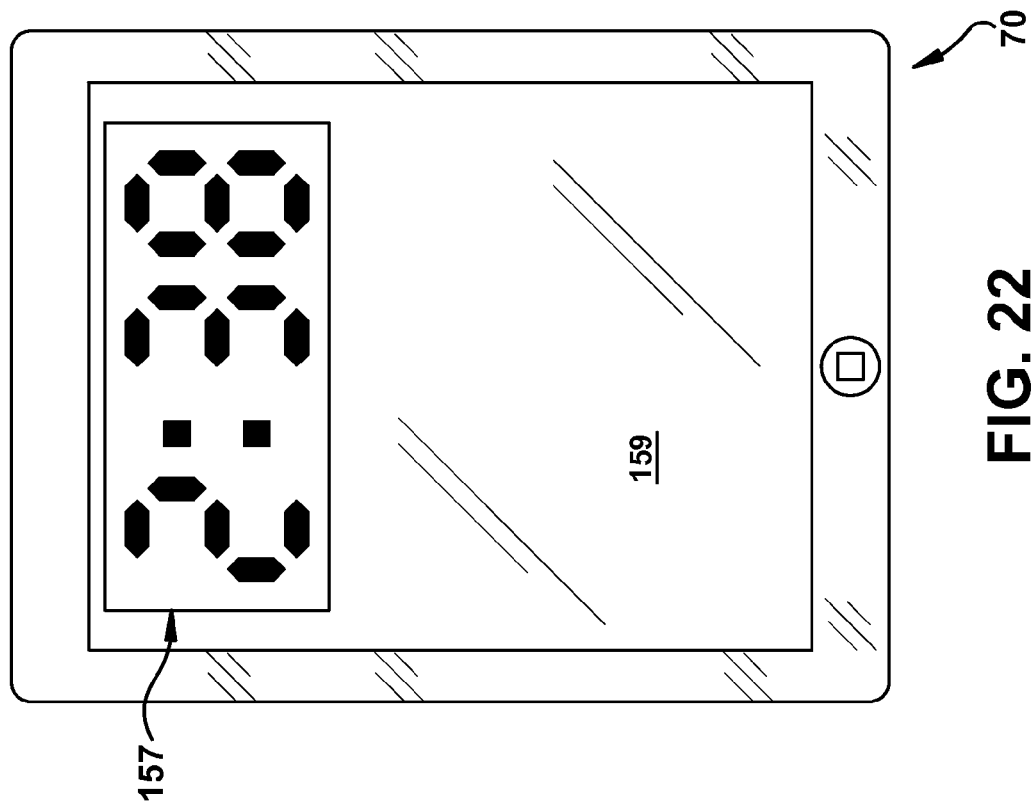
FIG. 22 shows an illustrative embodiment of a response exhibited by a tablet computer to receiving a communication from a sterilizer indicating that a decontamination process has been completed.

An example of such a response can include an audible and/or visible presentation via a speaker and/or display screen, respectively, provided to the tablet computer 70. As shown in FIG. 22, a timer 157 is displayed by a display screen 159, and counts down from a starting time, optionally concluding at zero or continuing to count down past zero to provide an onlooker with an indication of how long the countdown has been expired. The starting time can represent a length of time that the tablet computer 70, while remaining in the sleeve 72, can be considered suitably disinfected or sterile for use in the medical application before it must again be subjected to another decontamination process, which would reset the timer 157. The starting time can be established by the tablet computer 70, optionally based on information contained as part of the completion signal, or designated by the sterilizer 10 and transmitted to the tablet computer 70 in the completion signal. Embodiments of the timer 157 can include an audible and/or visible alert when the timer 157 has counted down to a predetermined time relative to zero (e.g., a one-minute warning), and optionally a different audible and/or visible alert when the timer 157 reaches zero.

Although the preceding embodiments describe the timer 157 as a countdown timer, other embodiments of the timer 157 can optionally count upward. Further, although the timer 157 is displayed by the display screen 159 in FIG. 22, the timer 157 can be hidden or minimized on the display screen 159 to avoid interfering with the ability of the user to utilize the tablet computer 70 to display content unrelated to the timer 157. In addition, the software application on the tablet computer can record, transmit, or display information related to the decontamination process, including but not limited to the decontaminating device, location of decontamination, time since decontamination, status of decontamination, number of decontamination processes, and the user performing decontamination process.

In other embodiments of the invention, the decontamination device can transmit information to the tablet computer indicating the operational status of the decontamination device including but not limited to the status of the decontamination source (e.g., bulb life and intensity of a UVC source), status of the transport mechanism, status of the enclosure (e.g., temperature or cover open), serial numbers of major components of the decontaminating device, decontamination cycles completed, decontamination cycles failed or aborted, records of items decontaminated, and diagnostic results from the device.

In other embodiments of the invention, the tablet computer can transmit information to the decontamination device that includes but is not limited to software updates for the decontamination device, date and time, loading and executing diagnostic software on the decontamination device, and configuration information of the decontamination device.

Figure 21:
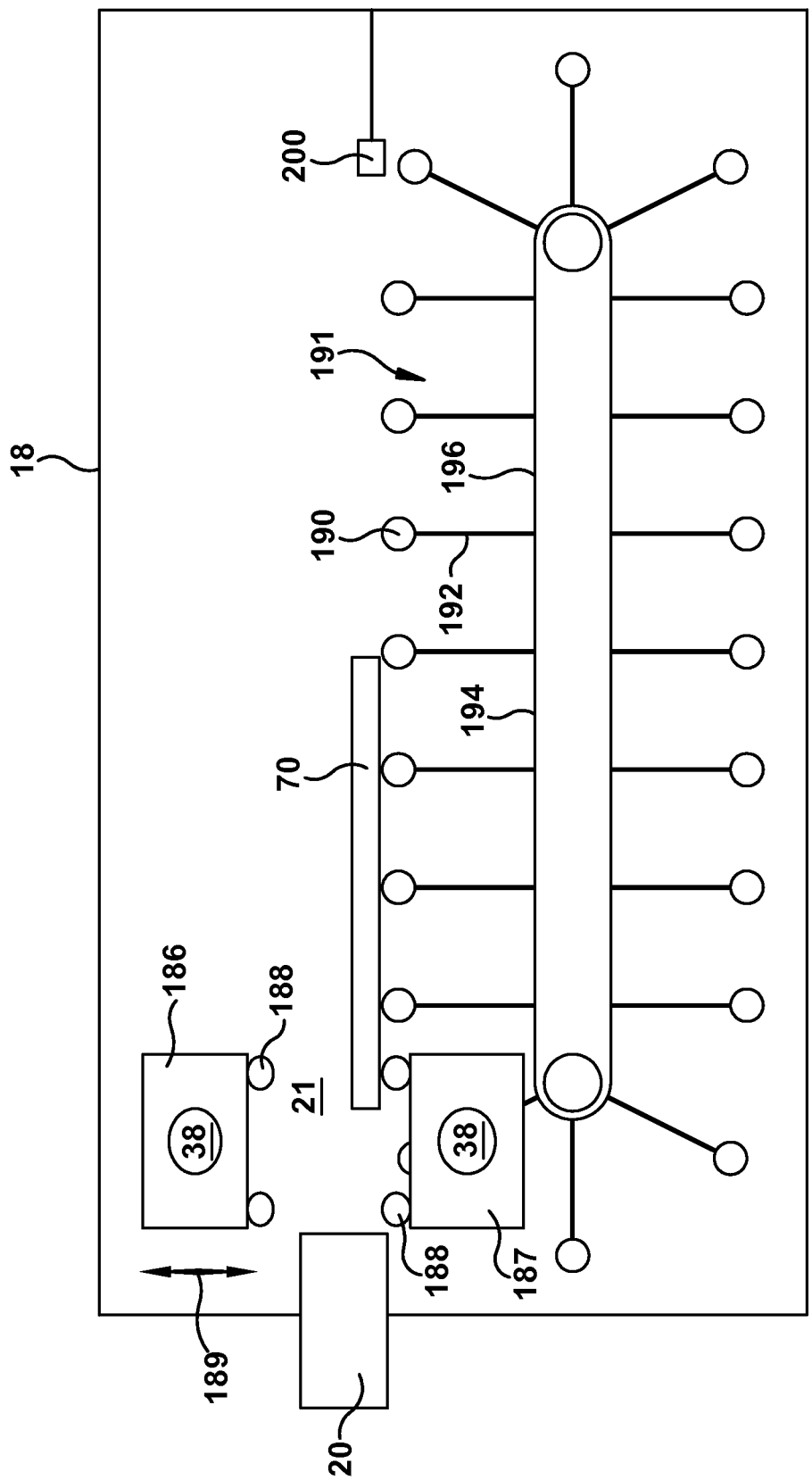
FIG. 21 shows illustrative embodiment of an alternate feeder configuration for transporting a tablet computer into and out of a sterilizer.

The embodiments described above have utilized sets of opposing rollers to convey the label 12, tablet computer 70 or other object past the lights 38 so portions of those objects are at least temporarily unsupported while being exposed to the lights 38 or other sterilizing agent. Another embodiment of a feeder for transporting objects in this manner is shown in FIG. 21. As shown in FIG. 21, the UVC lights 38 are each included in a light assembly 186, 187 that also supports a plurality of rollers 188. The lower light assembly 167 can be stationary, and positioned such that the rollers 188 provided thereto have an apex that is at approximately the same vertical elevation as the inlet aperture 20. As the tablet computer 70 is introduced to the inlet aperture 20, the leading end of the tablet computer 70 rolls over the rollers of the light assembly 187, and urges the other light assembly 186 upward, generally away from the first light assembly 187. The light assembly 186 can be adjustable in the directions indicated by arrow 189 such that the rollers 188 provided to that light assembly 186 roll over the tablet computer 70 as the tablet computer 70 is being inserted into the cabinet 18.

The tablet computer 70 is carried by a plurality of projections 191, each including a contact surface 190 supported atop a pillar 192 extending away from a continuous belt 196. When the tablet computer 70 reaches the point of full insertion, it contacts a plunger 200 that results in the transmission of a signal received by the controller 46 (FIG. 3) which, in turn, terminates operation of the motor 36 (FIG. 3) driving the belt 196. The light assemblies 186, 187 can be adjusted in planes substantially parallel to the major planer surfaces of the tablet computer 70 to expose an entire extent of the tablet computer 70 to UVC light. As the light assembly 187 passes under the tablet computer 70, it can make contact with the projections, causing them to be elastically repositioned so as to avoid shielding the underside of the tablet computer 70. At this time, the motor 36 is reversed, causing the belt to be driven in the opposite direction and the tablet computer 70 to be returned toward the inlet aperture 20. According to the present embodiment, portions of the tablet computer 70 passing by the lights 38 remain unsupported to avoid shielding portions of the tablet computer 70 from the UVC light.

In general, the embodiments of the sterilizer 10 described herein are not limited to sterilizing only the objects (e.g., label, tablet computer, etc. . . . ) specifically described. Further, although the feeder is specifically described as conveying the label 12 and tablet computer 70, alternate embodiments can optionally receive the object to be subjected to the decontamination process and adjust the position of the light(s) 38, the object, or both, relative to the other to expose an entirety of the object to the UVC light or other sterilizing agent. For such embodiments, the object can optionally be repositioned or otherwise adjusted during the decontamination process. Alternate embodiments of the sterilizer 10 can receive the object in a stationary position on a glass or other support that is substantially transparent to UVC light. Suitably arranged UVC lights can illuminate an entirety of the object resting on the glass or other support to the UVC light, a portion of which is transmitted through the glass or other suitable support without requiring the object to be conveyed or otherwise repositioned to expose all surfaces of the object to the UVC light.

Illustrative embodiments have been described, hereinabove. It will be apparent to those skilled in the art that the above devices and methods may incorporate changes and modifications without departing from the general scope of this invention. It is intended to include all such modifications and alterations within the scope of the present invention. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A method of using an object for a medical application, the method comprising:
    enclosing the object within a sleeve comprising a transparent portion through which the object within the sleeve is observable to render the object usable within the sleeve in a contagion-sensitive environment, wherein the object is an electronic device comprising a display screen, and said enclosing the electronic device within the sleeve comprises arranging the electronic device within the sleeve so the display screen is viewable through the transparent portion;
    introducing the electronic device enclosed within the sleeve to a decontamination chamber into which an ultraviolet light source emits ultraviolet light;
    exposing the sleeve enclosing the electronic device within the decontamination chamber to the ultraviolet light emitted by the ultraviolet light source;
    subsequent to said exposing the sleeve enclosing the electronic device to the ultraviolet light, obtaining the electronic device enclosed within the sleeve in a decontaminated state to be used for its intended purpose within the contagion-sensitive environment while the electronic device is enclosed within the sleeve; and
    after said obtaining the electronic device within the sleeve from the decontamination chamber in a decontaminated state, using the electronic device within the contagion-sensitive environment while the electronic device remains in the sleeve.

2. The method of claim 1 further comprising enclosing the electronic device enclosed within the sleeve within an additional sleeve that is substantially transparent to ultraviolet light.

3. The method of claim 2, wherein said enclosing the electronic device enclosed within the additional sleeve comprises inserting the electronic device enclosed within the sleeve into an opening provided to the additional sleeve and then closing the opening to interfere with removal of the electronic device enclosed within the sleeve from the additional sleeve.

4. The method of claim 2 further comprising extracting the electronic device enclosed within the sleeve from the additional sleeve so the electronic device can be used while enclosed within the sleeve.

5. The method of claim 1, wherein said enclosing the electronic device within the sleeve comprises inserting the electronic device through an opening defined by the sleeve and closing the opening to secure the sleeve.

* * * * *